(12) United States Patent
Wu et al.

(10) Patent No.: US 9,867,542 B2
(45) Date of Patent: Jan. 16, 2018

(54) TIME REVERSAL OPTICAL TOMOGRAPHY FOR LOCATING TARGETS IN A HIGHLY SCATTERING TURBID MEDIUM

(71) Applicant: Research Foundation of the City University of New York, New York, NY (US)

(72) Inventors: Binlin Wu, Forest Hills, NY (US); Wei Cai, Bronx, NY (US); Swapan K. Gayen, Marlboro, NJ (US)

(73) Assignee: Research Foundation of the City University of New York, New York, NY (US)

( * ) Notice: Subject to any disclaimer, the term of this patent is extended or adjusted under 35 U.S.C. 154(b) by 123 days.

(21) Appl. No.: 14/060,221

(22) Filed: Oct. 22, 2013

(65) Prior Publication Data
US 2014/0114181 A1    Apr. 24, 2014

Related U.S. Application Data

(60) Provisional application No. 61/716,762, filed on Oct. 22, 2012.

(51) Int. Cl.
*A61B 5/05*   (2006.01)
*A61B 5/00*   (2006.01)

(52) U.S. Cl.
CPC .......... *A61B 5/0073* (2013.01); *A61B 5/0071* (2013.01); *A61B 5/4312* (2013.01); *A61B 5/4381* (2013.01); *A61B 5/7225* (2013.01)

(58) Field of Classification Search
CPC ............ A61B 5/0073; G01N 21/4795; G01N 2021/1787
See application file for complete search history.

(56) References Cited

U.S. PATENT DOCUMENTS

2012/0236310 A1*  9/2012  Lesage et al. ................ 356/432

OTHER PUBLICATIONS

Cai, Three-dimensional optical tomography of objects in turbid media using the 'round-trip matrix' Proc. SPIE 5693, Optical Tomography and Spectroscopy of Tissue VI, 4 (May 5, 2005).*
Ntziachristos, Experimental three-dimensional fluorescence reconstruction of diffuse media by use of a normalized Born approximation, Jun. 15, 2001 / vol. 26, No. 12 / Optics Letters.*
(Continued)

*Primary Examiner* — Ellsworth Weatherby
(74) *Attorney, Agent, or Firm* — Peter J. Mikesell; Schmeiser, Olsen & Watts, LLP

(57) ABSTRACT

A time reversal optical tomography (TROT) method for near-infrared (NM) diffuse optical imaging of targets embedded in a highly scattering turbid medium is presented. TROT combines the basic symmetry of time reversal invariance and subspace-based signal processing for retrieval of target location. The efficacy of TROT is tested using simulated data and data obtained from NIR imaging experiments on absorptive, scattering and fluorescent targets embedded in Intralipid-20% suspension in water, as turbid medium, as well as, a realistic cancerous model breast assembled using ex vivo human breast tissues with two embedded tumors. The results demonstrate the potential of TROT for detecting and locating small targets in a turbid medium, such as, breast tumors in early stages of growth.

20 Claims, 11 Drawing Sheets

(56) References Cited

OTHER PUBLICATIONS

B. Wu, M. Alrubaiee, W. Cai, M. Xu, and S. K. Gayen, "Optical Imaging of Objects in Turbid Media Using Principal Component Analysis and Time Reversal Matrix Methods," in Frontiers in Optics 2009/Laser Science XXV/Fall 2009 OSA Optics & Photonics Technical Digest, OSA Technical Digest (CD) (Optical Society of America, 2009), paper JTuC10.*
Min Xu, Yang Pu, and Wubao Wang, "Clean image synthesis and target numerical marching for optical imaging with backscattering light," Biomed. Opt. Express 2, 850-857 (2011).*
Devaney, Anthony J. "Super-resolution Processing of Multi-static Data Using Time Reversal and Music." (2000).*
Devaney, A. J., "Super-Resolution Processing of Multi-static Data Using Time-Reversal and Music," Department of Electrical Engineering, Northeastern University, Boston, MA 02115, 25 pages.
Wu, Binlin; "Time reversal optical tomography: locating targets in a highly scattering turbid medium" Optics Express, v. 19, No. 22; Oct. 23, 2011.

* cited by examiner

TIME REVERSAL OPTICAL TOMOGRAPHY FOR LOCATING TARGETS IN A HIGHLY SCATTERING TURBID MEDIUM

CROSS-REFERENCE TO RELATED APPLICATIONS

This application claims priority to U.S. provisional patent application No. 61/716,762 (filed Oct. 22, 2012), the entirety of which is incorporated herein by reference.

BACKGROUND OF THE INVENTION

Optical imaging of targets embedded in a highly scattering turbid medium, such as, a tumor in a breast, is a challenging problem because light is strongly absorbed and scattered by the medium leading to poor signal-to-noise ratio, as well as, loss of phase coherence and polarization. As a consequence distinct, sharp image of the targets may not be formed directly. Various frequency-domain, time-resolved, and steady-state inverse image reconstruction (IIR) approaches are being pursued to form tomographic images using diffusively scattered light measured at the sample boundary. IIR is an ill-posed problem and the development of reliable and fast approaches remains a formidable task. Recent IIR algorithms, such as Newton-Raphson-Marquardt algorithms and direct linear inversion of 3-D matrices, are time consuming. The iterative methods may not ensure that the obtained result arrives at a "global minimum" or converges to a "local minimum." Still the potential for developing non-invasive imaging approaches with diagnostic ability motivates the ongoing diffuse optical tomography (DOT) research using NIR light.

Many applications require rather accurate determination of location of target(s) in three dimensions. For example, a recent study involving 35,319 patients underscores the influence of primary tumor location on breast cancer prognosis, and makes it imperative that DOT for breast cancer detection be able to obtain three-dimensional (3-D) location of the tumor. While two-dimensional (2-D) IIR approaches may provide only lateral positions, 3-D IIR approaches attempt to retrieve all three position coordinates of the target(s). Various frequency-domain, time-domain, and steady-state DOT approaches have addressed the target localization problem with different measures of success.

The discussion above is merely provided for general background information and is not intended to be used as an aid in determining the scope of the claimed subject matter.

BRIEF DESCRIPTION OF THE INVENTION

The present invention provides a time reversal optical tomography (TROT) approach for NIR optical imaging of target(s) in a turbid medium. The invention's initial results of its efficacy using both simulated and experimental data are demonstrated.

Time reversal (TR) invariance, the basic symmetry that commonly holds in microscopic physics, forms the basis for macroscopic TR imaging. TR imaging using the so-called "time-reversal mirrors" (TRMs) has been used as an experimental tool in acoustics with practical applications in medicine, underwater imaging, and nondestructive testing. The theoretical and numerical techniques involved in time reversal have been used for applications involving both acoustic waves and electromagnetic waves (radar).

Devaney and associates developed a theoretical framework for a TR imaging method with Multiple Signal Classification (MUSIC) for finding the location of scattering targets whose size is smaller than the wavelength of acoustic waves or electromagnetic waves (radar) used for probing the homogeneous or inhomogeneous background medium in which the targets were embedded. While their initial focus was on back-propagation geometry that used coincident acoustic or electromagnetic transceiver array for interrogating the targets, they later extended the formalism to transmission geometry where sources and detectors were distinct and separated. They also generalized the theory which was based on distorted wave Born approximation (DWBA) to account for multiple scattering between the targets. In its basic form TR-MUSIC found target location from knowledge of the response matrix K, which was constructed from multi-static data collected by the transceiver array. TR-MUSIC provided higher spatial resolution than the conventional TR imaging, especially in the case where targets were not well resolved.

The TR-MUSIC approach is herein adapted to the optical domain, i.e. to diffusive optical imaging for detecting and locating targets embedded in a turbid medium. TROT is described in detail using both simulated data and data from transillumination NIR imaging experiments in slab geometry. A TR matrix is obtained by multiplying the response matrix formed using experimental or simulated data to its adjoint. The leading non-zero eigenvalues of the Hermitian TR matrix determine the signal subspace due to presence of the targets. The signal subspace is separated from the noise subspace using an L-curve method. The vector subspace method, MUSIC, along with Green's functions calculated from an appropriate forward model for light propagation through the turbid medium is then used to determine the locations of the targets. The MUSIC algorithm judges if the calculated Green's function vector corresponding to a location in the sample is mapped into the signal subspace or the noise subspace.

Several salient features make TROT attractive and potentially more promising than other IIR methods. First the size of the TR matrix is much smaller than those used in other IIR approaches, which makes solution of the eigenvalue problem easier and faster. Second, to determine locations of targets, TR-MUSIC approach runs the program over all voxels only once, and there is no need to carry out an iterative procedure done by other inverse approaches. Other IIR approaches seek to determine the absorption and scattering parameters at all voxels into which the sample is divided. The process is iterative, computationally intensive, and leads to a non-unique solution of the inverse problem because the problem is ill-posed, even when there is no noise. In contrast, TROT seeks to determine the locations of the targets first and thereafter retrieve other information, such as, the size and optical properties of the limited number of targets in the medium, which requires significantly less computation time. The focus of this invention is on finding the locations of targets.

Our result using simulated data shows that without the presence of noise TROT determines the locations of the embedded targets accurately with high resolution. TROT exhibits promise to locate targets both in simulations and experiments even when substantial noise is present. Images of small targets obtained by this approach are sharper than that obtained by other IIR approaches.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 6A is experimental data, and FIG. 6B is a simulation with 20% Gaussian noise added. P is pseudo value calculated using Eq. (20);

DETAILED DESCRIPTION OF THE INVENTION

Figure 1A:
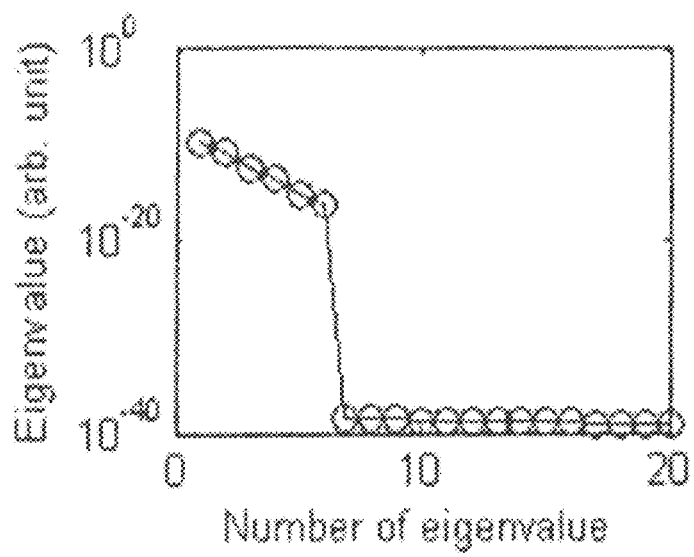
FIG. 1A is the plot of the first 20 eigenvalues while FIG. 1B a 2D slice plotted using the pseudo spectrum.

A method for optically imaging a turbid medium to locate one or more targets is provided. In one embodiment, the turbid medium is biological tissue (e.g. breast tissue) and the illumination source is light beam with near-infrared (NIR) wavelengths selected to fall within the biological window for the tissue being examined. Generally, the wavelength is between 600 nm and 1000 nm. The method is non-invasive, non-irradiative, can be accomplished with small, portable machines, is inexpensive and can, in certain embodiments, provide real-time imaging.

Diffusion Approximation, Perturbation Method and Response Matrix

The formalism of the TROT approach is now presented. The starting point for the TROT formalism is the diffusion approximation of the radiative transfer equation (RTE). The perturbation in the light intensity distribution due to small inhomogeneities (targets) embedded in a homogeneous medium, to the first order Born approximation, can be written as:

$$\Delta \phi(r_d, r_s) = -\int G(r_d, r)\delta\mu_a(r)cG(r, r_s)d^3r \qquad (1)$$
$$- \int \delta D(r)c\nabla_r G(r_d, r) \cdot \nabla_r G(r, r_s)d^3r,$$

where $r_s$, $r_d$ and $r$ are the positions of a point-like source of unit power, detector and target, respectively; $G(r,r_s)$ and $G(r_d,r)$ are the Green's functions that describe light propagations from the source to the target and from the target to the detector, respectively; $\delta\mu_a$ is the difference in absorption coefficient and $\delta D$ is the difference in diffusion coefficient between the targets and the background medium; and c is the light speed in the medium.

A multi-source interrogation and multi-detector signal acquisition scheme is used to acquire transillumination data, from which the difference in the light intensity distribution due to the targets, $\Delta\varphi=\varphi-\varphi_0$, is found where $\varphi$ is the light intensity distribution measured on the sample boundary with targets embedded in the scattering medium and $\varphi_0$ is ideally the light intensity distribution without the targets, which in practice is approximated by an "average" over all the multi-source measurements. A response matrix K is constructed with $-\Delta\varphi$, to describe the transport of light from different sources through the embedded objects to the array of detectors.

For small, point-like absorptive targets, the matrix elements can be rewritten in a discrete form as:

$$K_{ij} = \sum_{m=1}^{M} G^d(r_i, X_m)\tau_m G^s(X_m, r_j), \quad (2)$$

$$i = 1, 2, \ldots, N_d; j = 1, 2, \ldots, N_s,$$

where $\tau_m = \delta\mu_a(X_m)c\delta V_m$ is the optical absorption strength of the $m^{th}$ target, $\delta V_m$ is the volume of the $m^{th}$ target, $r_i$, $r_j$ and $X_m$ are locations of the $i^{th}$ detector, $j^{th}$ source and $m^{th}$ target, respectively. Due to the reciprocity of light propagation in the medium, $G(r,r')=G(r',r)$. Thus, $$K_{ij} = \sum_{m=1}^{M} G^d(X_m, r_i)\tau_m G^s(X_m, r_j) \quad (3)$$

and $$K = \{K_{ij}\} = \sum_{m=1}^{M} g_d(X_m)\tau_m g_s^T(X_m), \quad (4)$$

where $g_s(r)$ and $g_d(r)$ are Green's function vectors (GFVs) associated with the source array and detector array, respectively. GFVs are defined as:

$$g_s(r) = [G^s(r_1, r), G^s(r_2, r), \ldots, G^s(r_{N_s}, r)]^T, \quad (5a)$$

$$g_d(r) = [G^d(r_1, r), G^d(r_2, r), \ldots, G^d(r_{N_d}, r)]^T, \quad (5b)$$

where the superscription T denotes transpose; and $N_s$, $N_d$ and M are the numbers of sources, detectors and targets, respectively. It is assumed the number of targets is less than the number of sources and detectors, $M < \min(N_d, N_s)$. It also holds that $K^T = \{K_{ji}\}$ describes light propagation from the positions of detectors through the medium and targets to sources.

For a homogenous background medium, the rank R of matrix K, is equal to the dimension of the source array vector space $\mathcal{G}_s$ spanned by $g_s(r_m)$, and also equal to the dimension of the detector array vector space $\mathcal{G}_d$ spanned by $g_d(r_m)$, where $\mathcal{G}_s \subseteq \mathbb{C}^{N_s}$ and $\mathcal{G}_d \subseteq \mathbb{C}^{N_d}$. For absorptive targets, R is equal to the number of targets M.

Similar forms of the response matrix and GFVs can be obtained for scattering targets. As the dot product in the second term of Eq. (1) implied each scattering target is represented by three components coexisting at one location. The elements of the K matrix for L scattering target may be written as:

$$K_{ij} = \sum_{l=1}^{L} \tau_l \nabla_r G^d(r_i, X_l) \cdot \nabla_r G^s(X_l, r_j) \quad (6)$$

$$= \sum_{l=1}^{L} \tau_l \sum_{\alpha=\{x,y,z\}} \partial_\alpha G^d(r_i, X_l) \partial_\alpha G^s(X_l, r_j)$$

where $\tau_l = \delta D(X_l)c\delta V_l$ is the optical scattering strength of the $l^{th}$ target. The K matrix for scattering targets can be written in a manner similar to that for absorptive targets:

$$K = \sum_{l=1}^{L} \sum_{\alpha=\{x,y,z\}} \partial_\alpha g_d(X_l)\tau_l \partial_\alpha g_s(X_l). \quad (7)$$

The Green's function for a slab geometry is:

$$G(r, r') = G(r', r) = \frac{1}{4\pi D} \sum_{k=-\infty}^{\infty} \left( \frac{e^{-\kappa r_k^+}}{r_k^+} - \frac{e^{-\kappa r_k^-}}{r_k^-} \right), \quad (8a)$$

$$r_k^\pm = [(x-x')^2 + (y-y')^2 + (z \mp z' + 2kd)^2]^{1/2}, \quad (8b)$$

where $\kappa = [(\mu_a - I\omega/c)/D]^{1/2}$ in frequency domain with amplitude modulation frequency $\omega$, and $k = 0, \pm 1, \pm 2, \ldots$. The extrapolated boundaries of the slab are located at $z=0$ and $z=d=L+2z_e$, respectively, where L is the physical thickness of the slab and the extrapolation length $z_e$ is determined from the boundary condition of the slab.

Under ideal conditions, when all three scattering components of each of the L scattering targets are well-resolved, the rank of K contributed by L scattering targets is 3L. In practice, four components (one for absorption and three for scattering) are calculated for each target, since the targets may have both scattering and absorptive characteristics, or the exact nature may not be known a priori. The dominant characteristic is used to label the target as absorptive or scattering in nature.

Point Spread Functions

If light emitted by a source of unit power at target position X propagates in the sample medium, the signal measured by the detector array at the sample boundary is $G^d(r_i, X)$. The signal is then "time-reversed" and back-propagated with the Green's function of the background medium. TR operation is phase conjugation in Fourier domain. So the signal evaluated at r is:

$$H_d(r, X) = \sum_{i=1}^{N_d} G_d(r, r_i) G^{d*}(r_i, X) \quad (9)$$

$$= g_d^T(r) g_d^*(X)$$

$$= g_d^\dagger(X) g_d(r)$$

$$= \langle g_d(X), g_d(r) \rangle,$$

where * denotes the phase conjugate, † denotes adjoint, and $\langle \cdot \rangle$ denotes inner product. $H_d(r,X)$ is the detector array point spread function (PSF). A source array PSF can be similarly formed as:

$$H_s(r,X) = g_s(X)^\dagger g_s(r) = \langle g_s(X), g_s(r) \rangle. \quad (10)$$

Due to time reversal assumption, $H_d(r,X)$ peaks at $r=X$, so it can be considered as an image of the source at X formed by the TR detector array. PSF vanishes when r is far away from X. A similar interpretation can be used for $H_s(r,X)$.

Time Reversal and MUSIC

The TR matrix may be constructed to represent light propagation from sources to detectors and back to sources, denoted by $T_{SDDS}$, or to represent light propagation from detector positions to source positions and back to detectors, denoted by $T_{DSSD}$, a consequence of the reciprocity of light propagation. For frequency-domain data, $T_{SDDS} = K^\dagger K$ and $T_{DSSD} = (K^T)^\dagger K^T = K^* K^T$, where response data matrix K is formed using modulated intensities, instead of the field with phase information used in the conventional TR. For CW measurements, $T_{SDDS} = K^T K$, and $T_{DSSD} = KK^T$ (K is real and only includes intensity values).

Since $T_{SDDS}$ and $T_{DSSD}$ are Hermitian ($T^\dagger = T$), they have complete sets of orthonormal eigenvectors $v_j$ ($j=1, \ldots, N_s$)

and $u_i$ (i=1, ..., $N_d$), with a common set of non-negative real eigenvalues. For M<min($N_s$, $N_d$) absorptive targets without the presence of noise, the rank of $T_{SDDS}$ and $T_{DSSD}$ is M. The eigenvalues $\lambda_j>0$, when j=1, ..., M, and $\lambda_j=0$, when j=M+1, ..., $N_s$ for $T_{SDDS}$ and j=M+1, ..., $N_d$ for $T_{DSSD}$. The eigen system {$v_j$, $u_j$,$\lambda_j>0$}, j=1, ..., M, is related to the targets. The TR matrix $T_{SDDS}$ can be written as:

$$T_{SDDS} = \sum_{m=1}^{M} \sum_{m'=1}^{M} \tau_m^* \tau_{m'} \langle g_d(X_m), g_d(X_{m'}) \rangle g_s^*(X_m) g_s^T(X_{m'}). \quad (11)$$

Subsequent formalism may be different depending on whether the targets are "well resolved" or "poorly resolved."

Well-Resolved Targets

If the $m^{th}$ and $m'^{th}$ targets (m≠m') are well resolved, defined by the conditions:
$H_s(X_m,X_{m'})\approx 0$ and $H_d(X_m,X_{m'})\approx 0$, i.e. the GFVs at $X_m$ and $X_{m'}$ are orthogonal, $\langle g_d(X_m),g_d(X_{m'})\rangle = H_d(X_m,X_{m'}) = \|g_d(X_m)\|^2 \delta_{mm'}$. So we have:

$$T_{SDDS} = \sum_{m=1}^{M} |\tau_m|^2 \|g_d(X_m)\|^2 g_s^*(X_m) g_s^T(X_m), \quad (12)$$

where $\|\bullet\|$ denotes L2 norm. The eigenvectors of $T_{SDDS}$ are proportional to the phase conjugate of the GFVs associated with the M targets, i.e.:

$$T_{SDDS} g_s^*(X_m) = |\tau_m|^2 \|g_d(X_m)\|^2 \|g_s(X_m)\|^2 g_s^*(X_m). \quad (13)$$

The eigenvectors are:

$$v_j = \frac{g_s^*(X_j)}{\|g_s(X_j)\|}, \quad (14)$$

with eigenvalues $\lambda_j = |\tau_j|^2 \|g_d(X_j)\|^2 \|g_s(X_j)\|^2$, j=1, ..., M. Thus $T_{SDDS}$ is a projection operator that projects a vector onto the conjugate of the source array vector space $\mathcal{G}_s$. The $j^{th}$ non-zero eigenvalue $\lambda_j$ is directly related to the optical strength $\tau_j$ of the $j^{th}$ target. Similar equations can be derived for $T_{DSSD}$, which is a projection operator for the conjugate of the detector array vector space $\mathcal{G}_d$. The eigenvectors of $T_{DSSD}$ are:

$$u_j = \frac{g_d^*(X_j)}{\|g_d(X_j)\|}, \quad (15)$$

j=1, ..., M, with the same eigenvalues as $T_{SDDS}$.

Therefore, for well-resolved targets, the target locations can be determined by the inner product:

$$\psi_j^s = \langle v_j^*, g_s(X_p) \rangle \quad (16a)$$
$$= v_j^T g_s(X_p)$$
$$= \frac{g_s^\dagger(X_j)}{\|g_s(X_j)\|} g_s(X_p)$$
$$= \frac{1}{\|g_s(X_j)\|} H_s(X_p, X_j),$$

or $$\psi_j^d = \langle u_j^*, g_d(X_p) \rangle \quad (16b)$$
$$= u_j^T g_d(X_p)$$
$$= \frac{g_d^\dagger(X_j)}{\|g_d(X_j)\|} g_d(X_p)$$
$$= \frac{1}{\|g_d(X_j)\|} H_d(X_p, X_j),$$

where $X_p$ is a test target position, which is the position of any voxel in the sample space. $\psi_j^s$ and $\psi_j^d$ peak when $X_p$ is the position of the $j^{th}$ target. In classical TR imaging, for ideally resolved targets, each eigenvector of the TR operator can be used to focus on one particular target. Here $\psi_j^s$ and $\psi_j^d$ represent focusing of signals from the source and detector planes on to the target position, respectively. Use of the eigenvectors $v_j$ and $u_j$, j=1, ..., M, ensures that the $j^{th}$ target is sorted out. When $T_{SDDS}$ and source array vector space ($T_{DSSD}$ and detector array vector space) are used, we call the scheme SDDS (DSSD). Both source and detector arrays can be considered simultaneously to locate the target by calculating:

$$\psi_j = \psi_j^d \psi_j^{s\dagger} = \frac{1}{\|g_d(X_j)\| \cdot \|g_s(X_j)\|} H_d(X_p, X_j) H_s^*(X_j, X_p), \quad (17)$$

j=1, ..., M, which is computationally equivalent to a process that light emitted from a virtual source of unit power at a test target position $X_p$, propagates to the TR source array and back to a true target position $X_j$; then it is re-emitted and further propagates to the TR detector array and back to the original position $X_p$. $\Psi_j$ peaks when the test target position $X_p$ coincides with the true target position $X_j$ associated with the $j^{th}$ eigenvector.

Poorly-Resolved Targets and MUSIC

When the targets are too close to each other or the sources and/or detectors are significantly sparse, the targets are considered to be poorly resolved and the GFVs at $X_m$ and $X_{m'}$ are not orthogonal. In such cases, the eigenvectors $v_j$ and $u_j$ do not correspond one-to-one with the GFVs associated with target positions $X_m$ (j, m=1, ..., M). The image resolution degrades because of contributions from multiple targets. To solve this problem, the subspace-based method, MUSIC was implemented with TR. MUSIC algorithm is based on the idea that although the vectors characterizing the targets are no longer orthogonal with each other, they are all located in the signal subspace, which is orthogonal to the noise subspace.

The orthonormal sets {$v_j^*$}(j=1, ..., $N_s$) and {$u_j^*$} (j=1, ..., $N_d$) span the spaces $C^{N_s}$ and $C^{N_d}$ associated with the source and detector arrays, respectively. While {$v_j^*$} and {$u_j^*$} with $\lambda_j>0$, form the signal subspaces on the source and detector arrays, $\mathcal{S}^s=\{v_j^*\}$ and $\mathcal{S}^d=\{u_j^*\}$ (j=1, ..., M), respectively; {$v_j^*$} and {$u_j^*$}, with $\lambda_j\approx 0$, form the noise subspaces $\mathcal{N}^s=\{v_j^*\}$ (j=M+1, ..., $N_s$) and $\mathcal{N}^d=\{u_j^*\}$ (j=M+1, ..., $N_d$), respectively. Thus $C^{N_s}=\mathcal{S}^s \oplus \mathcal{N}^s$ and $C^{N_d}=\mathcal{S}^d \oplus \mathcal{N}^d$. Since the dimension of the signal subspaces $\mathcal{S}^s$ and $\mathcal{S}^d$ and of the GFV spaces $\mathcal{G}_s$ and $\mathcal{G}_d$ are all equal to M, $\mathcal{G}_s \equiv \mathcal{S}^s$ and $\mathcal{G}_d \equiv \mathcal{S}^d$. The GFVs, $g_s(X_m)$ and $g_d(X_m)$, m=1, ..., M, are linear combinations of $v_j^*$ and $u_j^*$, j=1, ..., M, respectively. Therefore, $g_s(X_m) \in \mathcal{S}^s$ and $g_d(X_m) \in \mathcal{S}^d$, m=1, ..., M, associated with $m^{th}$ target are orthogonal to $v_j^* \in \mathcal{N}^s$ (j=M+1, ..., $N_s$) and $u_j^* \in \mathcal{N}^d$ (j=M+1, ..., $N_d$), respectively:

$$\langle v_j^*, g_s(X_m) \rangle = v_j^T g_s(X_m) \approx 0, j=M+1, \ldots, N_s, \quad (18a)$$

$$\langle u_j^*, g_d(X_m) \rangle = u_j^T g_d(X_m) \approx 0, j=M+1, \ldots, N_d, \quad (18b)$$

The locations of targets can be determined by calculating the following squared sum of inner products:

$$Q_s(X_p) = \sum_{j=M+1}^{N_s} |v_j^T g_s(X_p)|^2, \quad (19a)$$

$$Q_d(X_p) = \sum_{j=M+1}^{N_d} |u_j^T g_d(X_p)|^2. \quad (19b)$$

$Q_s(X_p)$ and $Q_d(X_p)$ vanish when the test target position $X_p$ is a true target position. Similar to Eq. (17), $Q=Q_s Q_d$ can be calculated with both source and detector arrays considered simultaneously. An alternative approach to accentuate a target position is to plot a pseudo spectrum defined as:

$$P_s(X_P) = \|g_s(X_p)\|^2 / |Q_s(X_p)| \quad (20a)$$

associated with the source array, or $$P_d(X_p) = \|g_d(X_p)\|^2 / |Q_d(X_p)| \quad (20b)$$

associated with the detector array, or $$P(X_p) = P_s(X_p) P_d(X_p) \quad (20c)$$

associated with both source and detector arrays, where $\|g_s(X_p)\|^2$ and $\|g_d(X_p)\|^2$ are used for normalization. The poles of the pseudo spectrum correspond to target locations. These MUSIC pseudo spectra can also be used to locate well-resolved targets.

Since the dimensions of the signal subspace is generally much smaller than that of the noise subspace, it is preferred that in Eq. (19) and Eq. (20), the signal subspace is used rather than the noise subspace for ease of computation. Using the properties of the projection operators associated with the source and detector arrays, $Q_s(X_p)$ and $Q_d(X_p)$ can be calculated as:

$$Q_s(X_p) = \|g_s(X_p)\|^2 - \sum_{j=1}^{M} |v_j^T g_s(X_p)|^2, \quad (21a)$$

$$Q_d(X_p) = \|g_d(X_p)\|^2 - \sum_{j=1}^{M} |u_j^T g_d(X_p)|^2. \quad (21b)$$

When the targets are embedded in a non-uniform medium, or when there is significant noise present, the noise or false targets contribute significantly to the eigenvalues. The near-zero and non-zero eigenvalues are not as well separated as when there are no noise. In this case, the rank of the TR matrix is larger than the number of targets M. The TR matrix may even be full rank. However, as long as M is less than $\min(N_s,N_d)$ and eigenvalues contributed by the noise and false targets are smaller than those contributed by the real targets with a threshold, the target positions can be obtained using a pseudo spectrum associated with the source array:

$$P_s(X_P) = \|g_s(X_p)\|^2 / |Q_s(X_p)_{\lambda_j \leq \epsilon}|, \quad (22)$$

where $Q_s(X_p)_{\lambda_j \leq \epsilon} = \|g_s(X_p)\|^2 - \Sigma_{\lambda_j > \epsilon} |v_j^T g_s(X_p)|^2$. Pseudo spectra associated with the detector array or with both source and detector arrays can also be obtained similarly. In practice, the threshold is selected to separate the signal and noise subspaces using a method similar to L-curve regularization.

When scattering targets are concerned, the GFVs $\partial_\alpha g$ ($\alpha$=x, y, z), associated with the test target position $X_p$ will be used to calculate the pseudo spectrum. For a target with both absorption and scattering properties at the wavelength of probing light, one GFV corresponding to absorption constructed as g and three GFVs corresponding to scattering target constructed with $\partial_\alpha g$ ($\alpha$=x, y, z) are used to calculate the pseudo spectrum over every voxel. Ideally, for an absorptive and scattering target four pseudo-values will be obtained for every target position. If the dominant value corresponds to the absorptive (any of the scattering) GFV, the target will be identified as absorptive (scattering) in nature.

Algorithm

Implementation of TROT to locate targets embedded in a highly scattering turbid medium involves the steps outlined below. For simplicity, the sizes of source array and detector array are assumed to be the same, i.e., $N_d = N_s = N$.

Step A: A response matrix K with size N×N is constructed using experimental data (or estimated data in simulation). Data comprises the perturbations in the light intensity distribution due to the targets, $\Delta\varphi = \varphi - \varphi_0$, where $\varphi$ is the light intensity distribution measured on the sample boundary with targets embedded in the scattering medium and $\varphi_0$ is ideally the light intensity distribution without the targets. In practice, $\varphi_0$ is approximated by an "average" over all the multi-source measurements, while in simulation it can be estimated without such approximation.

Step B: A detector array TR matrix, $T_{DSSD} = KK^T$ with size N×N for CW measurements is constructed. All the eigenvalues and the eigenvectors of the $T_{DSSD}$ matrix are computed. The eigenvectors are orthogonal to each other. It is to be noted that in this procedure we only deal with a matrix of dimension N, not a matrix of dimension of N×N as done in traditional inverse procedures.

Step C: The non-zero eigenvalues of $T_{DSSD}$ belonging to the signal subspace are separated from the near-zero eigenvalues belonging to the noise subspace using the L-curve method.

Step D: MUSIC approach is next used to determine the locations of the targets as follows. (i) The 3-D medium is divided into a certain number of voxels. A detector array GFV, $g_d(X_p)$, associated with an absorptive test target position $X_p$ at $p^{th}$ voxel is calculated using Diffusion Approximation of RTE. Other proper forward models could be used as well. In order to check if $g_d(X_p)$ is located in the signal subspace or in the noise subspace, a pseudo spectrum associated with the detector array is computed using Eq. (20b), where M is the dimension of the signal subspace found in step (c). If $g_d(X_p)$ is located in the signal subspace, the corresponding pseudo value $P(X_p)$ in Eq. (20b) will become a maximum. (ii) Pseudo spectra are also calculated using the other three GFVs, $\partial_\alpha g_d(X_p)$ ($\alpha$=x, y, z) for scattering property. (iii) All pseudo values are put together and sorted in a descending order. Since the leading pseudo values at $X_p$ are associated with targets and specific GFVs, the positions of the embedded targets and their nature (absorptive or scattering) are determined. The pseudo spectrum in the whole sample space can be used to plot pseudo tomographic images.

In this approach, only a single run is needed for calculating the pseudo spectrum and no iterative procedure is involved, which makes it faster and computationally less intensive than the traditional IIR approaches. Similar procedure can be used for application of TROT when $N_d \neq N_s$.

The pseudo spectrum associated with either the source array, or the detector array, or both source and detector arrays, as outlined in Eq. (20) can be used to obtain target positions.

It is instructive to compare the computational complexity of TROT formalism with that of typical iterative methods. For a typical iterative method, an equation b=Wx is solved to find the inhomogeneities (targets), where W is a weight matrix with size $N_d N_s \times N$, N is the number of voxels, b is an $N_d N_s \times 1$ vector describing the perturbation in the detected light intensity due to the presence of inhomogeneities, and x is the perturbation or variation in the optical properties from the background values with dimension of $N \times 1$. The computational complexity is typically $O(N_d N_s N^2)$ for a single iteration. The computational complexity of TROT is much smaller than that for even one iteration of an iterative method. For the SDDS scheme, the complexity for TROT is $O(N_d N_s^2)$ if $N_d N_s > NN_k$, and $O(N_s NN_k)$ otherwise, where $N_k$ is the dimension of the signal subspace. In the DSSD scheme, the complexity is $O(N_s N_d^2)$ if $N_d N_s > NN_k$, and $O(N_d NN_k)$ otherwise. TROT does not involve any iteration.

Fluorescent Targets

The theoretical formalism for fluorescence TROT considers fluorescent target(s) embedded in a highly scattering medium being diffusely excited by diffusely propagating light of wavelength $\lambda_x$, and detection of fluorescence emitted by the targets at wavelength $\lambda_m$, as a coupled diffuse transmission problem. Assuming fluorescent targets are localized, that is, the $j^{th}$ target is contained in volume $V_j$ centered at $r_j$, the fluorescence signal under illumination by a point source of unit power at $r_s$ is given by $$K = \sum_j g_d(r_j, \omega) f_j(\omega) g_s^T(r_j, \omega), \quad (23)$$

where $g_s(r, \omega) = \{G_x(r, r_s, \omega)\}^T$ and $g_d(r, \omega) = \{G_m(r_d, r, \omega)\}^T$, (the superscript $T$ denotes transpose) are Green's function vectors; $G_x(r, r_s, \omega)$ is a Green's function that describes light propagation at excitation wavelength $\lambda_x$ from the source at $r_s$ to the target at r; $G_m(r_d, r, \omega)$ is a Green's function that describes the propagation of fluorescent light at emission wavelength $\lambda_m$ from the target at r to the detector at $r_d$; $\omega$ is the modulation angular frequency of the light; $f_j(\omega)$ represents the fluorescence strength of the $j^{th}$ target, given by, $$f_j(\omega) = \gamma(r_j) c_m V_j / [1 - i\omega\tau(r_j)], \quad (24)$$

where $\gamma$ is the fluorescence yield, $c_m$ is the speed of light in the medium, and $\tau$ is the fluorescence lifetime. K describes the diffuse propagation of the excitation light of wavelength, $\lambda_x$, from the sources through the medium to the targets, and then the propagation of fluorescence of wavelength, $\lambda_m$ from the targets to the detectors. $K^T$ describes the virtual process of fluorescent light propagation from the positions of detectors to the targets, and then the propagation of the excitation light of wavelength $\lambda_x$, from the positions of the targets to the sources. A time reversal matrix $T_{SDDS} = K^\dagger K [T_{DSSD} = (K^T)^\dagger K^T = K^* K^T]$ in frequency domain is then constructed, where the superscript $\dagger$ denotes Hermitian conjugate, or $T_{SDDS} = K^T K$ ($T_{DSSD} = KK^T$) when using the continuous wave (CW) illumination, i.e. $\omega = 0$. $T_{DSSD}$ and $T_{SDDS}$ have eigenvectors $\{u_k, k=1, \ldots, N_d\}$ and $\{v_l, l=1, \ldots, N_s\}$, respectively, with a common set of eigenvalues $\{\mu_j, j=1, \ldots, \min(N_s, N_d)\}$, where $N_s$ and $N_d$ are numbers of sources and detectors, respectively. If the fluorescent targets are well resolved, the eigenvalues are, $\mu_j = |f_j|^2 \|g_d(r_j, \omega)\|^2 \|g_s(r_j, \omega)\|^2$; otherwise, they are linear combinations of the fluorescence strengths, similar to what is the case for absorptive and scattering targets.

The eigenvectors are separated into signal and noise subspaces using an L-curve method with an eigenvalue threshold $\epsilon$. The locations of targets are poles of the MUSIC pseudo spectrum $$P_d(X_p, \omega) = \|g_d(X_p, \omega)\|^2 \bigg/ \bigg| \|g_d(X_p, \omega)\|^2 - \sum_{\mu_j > \epsilon} |u_j^T g_d(X_p, \omega)|^2 \bigg|, \quad (25)$$

associated with the detector plane; $X_p$ spans probable target locations. A similar pseudo spectrum for the source plane $P_s(X_p, \omega)$, or the product of the two, $P(X_p, \omega) = P_s(X_p, \omega) P_d(X_p, \omega)$, may also be used to retrieve the target position. In this work, we used the pseudo spectrum, $P_d$ associated with the detector plane because: (a) the images naturally reside in the co-ordinate system based on the field of view of the charge-coupled device (CCD) camera (detectors) making data analysis easier; and (b) the use of many more detectors than sources in our experimental arrangement provides a more robust data set for superior noise-resistant and artifact-tolerant reconstruction in the detector plane than the source plane. We set $\omega = 0$ as a CW laser beam was used in the experiment.

Example 1—Testing TROT with Simulated Data

To test the efficacy of the TROT approach, we first consider a rather challenging task of detecting and locating six targets embedded in a simulated sample which is a 40-mm thick uniform scattering slab. Its absorption and diffusion coefficients are $\mu_a = 1/300$ mm$^{-1}$ and D=1/3 mm, respectively. The incident CW beam was step-scanned in an x-y array of 41×41 grid points with a step size of 2 mm on the input plane covering an 80 mm×80 mm area. Light transmitted from the opposite side (output plane) was recorded at 41×41 grid points covering the same area. No random noise was added.

The six (M=6) point-like absorptive targets, with absorption coefficient difference of $\Delta\mu_a = 0.01$ mm from the background, were placed at A (24 mm, 26 mm, 9 mm), B (38 mm, 38 mm, 15 mm), C (38 mm, 38 mm, 21 mm), D (40 mm, 38 mm, 21 mm), E (44 mm, 42 mm, 21 mm) and F (30 mm, 30 mm, 31 mm), respectively. The origin (0 mm, 0 mm, 0 mm) was located at the upper-left corner of the input boundary (source plane) of the sample. The medium was divided into 40×40×20 voxels, with each voxel of size 2 mm×2 mm×2 mm. As can be seen from the assigned coordinates, targets C and D are located at two adjacent voxels, and are close to target E, and these three targets are located in the same z-layer. Consequently, targets C and D are expected to be very difficult to resolve, and hard to distinguish from target E. Target B and C have the same lateral position x and y, and different depths. Target A is close to the source plane, while F is close to the detector plane.

Using the Diffusion Approximation of the RTE as the model for light propagation in slab geometry, signals arising from light propagation from the source array to the detector array through medium with and without the targets were calculated. The difference between the two sets, which is the perturbation due to the targets, was used as the "simulated data". The size of the K matrix is N×N=1681×1681. The TR matrix $T=KK^T$ was constructed. Then, 1681 eigenvalues and 1681 eigenvectors of T were found.

The first seven computed eigenvalues in a descending order of magnitude are listed in the first column of Table 1. The leading twenty eigenvalues are plotted in FIG. 1A on a logarithmic scale. The first six eigenvalues are at least 10 orders-of-magnitude higher than the 7-th and other smaller eigenvalues. Hence, the dimension of the signal subspace and the number of targets are determined to be six. The pseudo spectrum (consisting of 40×40×20×4 elements) was calculated using the M eigenvectors in the signal subspace. The values of elements in the pseudo spectrum were sorted in a descending order. The seven leading pseudo values are listed in Table 1 with the corresponding positions of voxels. The six peaks are found to be associated with the GFVs for absorptive targets. Namely, the corresponding six targets are identified to be absorptive targets.

Figure 1B:
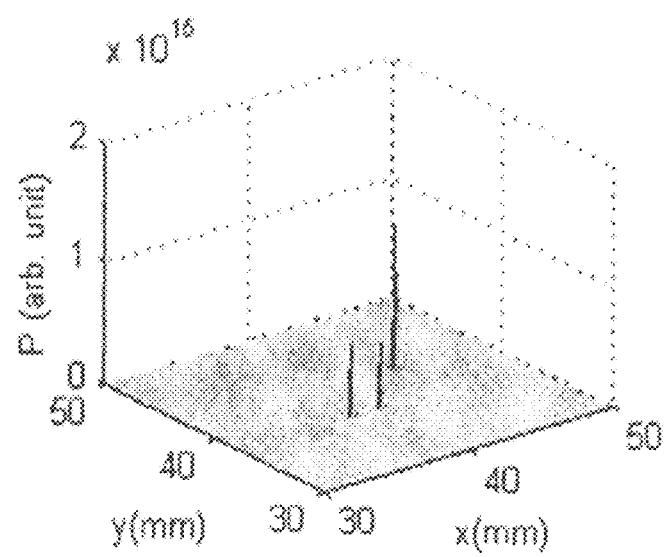

All six large pseudo-values are located at the exact known target locations and their values are approximately 9 orders-of-magnitude larger than those at their neighborhood locations. A 2-D slice of the pseudo spectrum on z=21 mm plane is shown in FIG. 1B, showing the locations of the three difficult targets.

TABLE 1

Eigenvalues, pseudo spectrum and the corresponding positions

| Leading Eigenvalues | Poles of Pseudo Spectrum | Retrieved Position (x, y, z) mm | Known Position (x, y, z) mm |
|---|---|---|---|
| 2.6697E−010 | 1.5911E+015 | (44, 42, 21) | (44, 42, 21) |
| 1.1722E−011 | 8.6376E+014 | (38, 38, 15) | (38, 38, 15) |
| 4.0081E−013 | 7.9559E+014 | (38, 38, 21) | (38, 38, 21) |
| 3.6676E−014 | 7.2328E+014 | (40, 38, 21) | (40, 38, 21) |
| 5.2629E−016 | 6.3010E+014 | (24, 26, 9) | (24, 26, 9) |
| 6.4837E−017 | 2.1159E+014 | (30, 30, 31) | (30, 30, 31) |
| 2.8337E−039 | 2.4353E+005 | (38, 38, 19) | |
| ... | ... | | |

With the highly encouraging result from simulation even for a considerably challenging task, we proceeded to test the approach for the realistic situation of detecting and locating targets from experimental data.

Testing TROT Using Experimental Data

Three different experiments with three different samples were carried out to test the efficacy of the TROT approach in detecting and locating targets in a turbid medium. All three samples used a 250 mm×250 mm×60 mm transparent plastic container filled with intralipid-20% suspension in water as the background medium. The concentration of Intralipid-20% was adjusted to provide an estimated absorption coefficient $\mu_a \sim 0.003$ mm$^{-1}$ at 790 nm, and a transport mean free path ~1 mm, which were similar to the average values of those parameters for human breast tissue, while the cell thickness of 60 mm was comparable to thickness of a typical compressed breast.

In the first experiment, the depth (position along z-axis) of an absorptive target was varied to explore how the accuracy of position estimate depended on depth. The target was a glass sphere of diameter ~9 mm filled with ink dissolved in Intralipid-20% suspension in water ($\mu_s$, was adjusted to be the same as that of the background medium, while $\mu_a \approx 0.013$ mm$^{-1}$ was about three times higher than that of background medium).

In the second experiment, the separation between two absorptive targets was varied to test how close those could be and yet be resolved as separate objects. Both the targets were similar to the target in the first experiment.

In the third experiment, the depth of a scattering target was varied to explore the efficacy of TROT in locating and characterizing a scattering target. The target was a glass sphere of diameter 10 mm filled with Intralipid-20% suspension in water to provide a transport mean free path of 0.25 mm, and a scattering coefficient $\mu_s \approx 11$ mm$^{-1}$.

Figure 2:
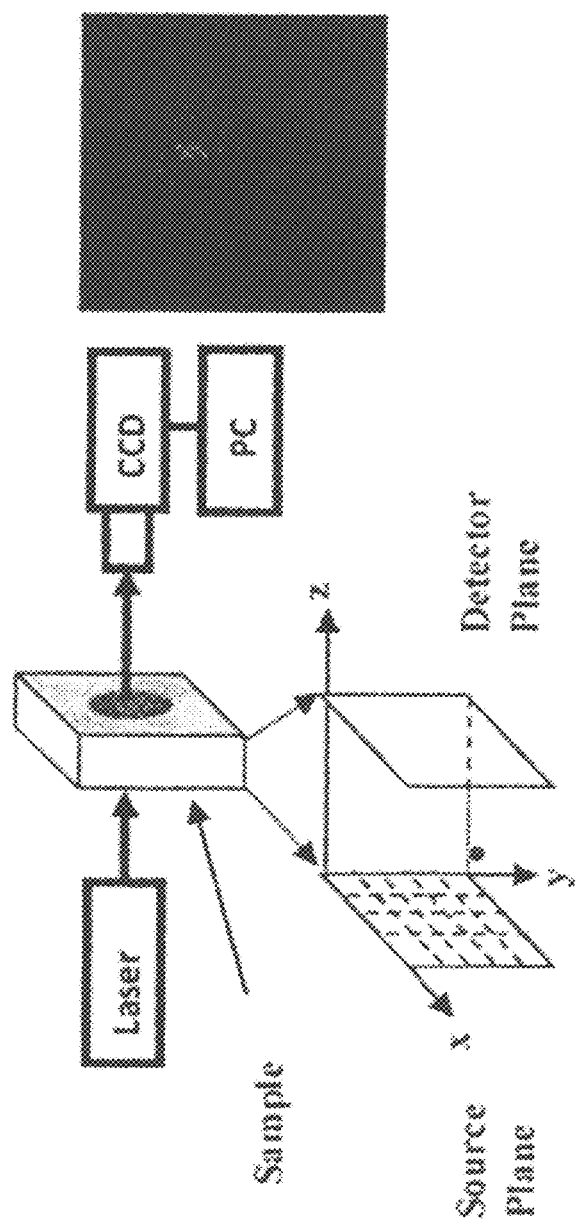
FIG. 2 is a schematic diagram of the experimental arrangement for imaging objects.

A multi-source interrogation and multi-detector signal acquisition scheme, shown in FIG. 2, was used to acquire data. A 100-mW 790-nm diode laser beam was used to illuminate the samples. A 1024×1024 pixels charge coupled device (CCD) camera equipped with a 60-mm focal-length camera lens was used on the opposite side of the sample to detect the transmitted light on the boundaries of the slab samples (detector plane). The pixel size was 24 μm. The multi-source illumination scheme was realized by scanning the sample across the laser beam in a two-dimensional x-y array of grid points using a computer-controlled translation stage. The first and third samples were scanned across the laser beam in an array of 9×9 grid points, and the second sample was scanned in an array of 15×11 grid points, with a step size of 5 mm in all cases. The scanning and data acquisition processes were controlled by a personal computer (PC). Raw transillumination images of the sample were recorded by the PC for each scan position, and stored for subsequent analysis. A typical image, which is a 2-D intensity distribution, is shown in the right side of FIG. 2.

While we have scanned the sample and kept the source fixed in the experiments reported here, a more clinically relevant approach would be to scan the source and fix the sample. In the experimental arrangement, the source scanning may be accomplished by: (a) delivering the beam using an optical fiber, and translating the delivery end of the fiber in an x-y array using a computer-controlled translation stage; or (b) raster scanning the laser beam using two orthogonal (x-y) galvanometers. The main change in the processing of data would involve alignment of the images so that laser beam positions are overlapped before averaging to generate the background image.

Data Processing and Analysis

From each image, a region of interest was cropped out and then every 5×5 pixels in the cropped image were binned to one pixel to enhance the signal-to-noise ratio. The background image was generated by taking an average of the original images for all scan positions, which is a reasonable approximation since for most of the scan positions the target(s) is (are) not along the direction of the incident beam. Then the background image was also cropped and binned corresponding to the region of interest for each scan position. Perturbation in the light intensity distribution Δφ due to targets in each image was found by subtracting the background image from each individual image. The response matrix was constructed using the light intensity perturbations, −Δφ. The TR matrix was generated by multiplying the response matrix by its transpose for our continuous-wave (CW) probing scheme. The eigenvalue equation was solved and the signal subspace was selected and separated from the noise subspace. MUSIC was then used to calculate the pseudo spectrum for all voxels in the 3-D space of the sample. For each voxel, four pseudo values, one for absorption and three for scattering as described in Algorithm step (d), were calculated. The voxel size was 0.77 mm×0.77 mm×1 mm. By sorting the pseudo spectrum in a descending order, the target(s) were located.

The voxel size to be used in reconstruction and its relation to the target size is an important consideration. In general, smaller voxels provide reconstruction of higher resolution at the cost of increased computational time. Finer details of an extended target may be obtained using smaller voxels. Decreasing the voxel size indefinitely may not improve resolution because of the diffusive nature of light propagation in the turbid medium. However, the computation time increases dramatically, which has been observed by other researchers. The optimal voxel size for a given reconstruction problem will depend on factors, such as, target size, experimental geometry, and noise level.

Since the signal used in image reconstruction is taken to be the difference between the image recorded for a scan position and the background image, estimation of the background image is an important issue. This is a common problem for every diffuse optical imaging modality using perturbation method, and needs further elaboration. We accumulated data in the transillumination slab geometry, and generated the background image by averaging images for all scan positions after proper alignment with respect to the incident source position. This averaging method for generating background image worked well for small targets that we used in our experiments, as the ratio of sample volume to target volume was quite high (~500:1). This volume ratio for breast and a tumor in early stages of growth will also be substantially high for the averaging method to be applicable. Assuming a scenario where the volume ratio is substantially smaller than in above examples, a modified approach would be to select recorded images which were minimally affected by embedded targets for averaging. As long as the targets only occupy a limited volume within the host medium, a clean background image can be generated in this fashion. It should also be noted that while estimation of target optical properties, such as absorption coefficient and scattering coefficient, are sensitively dependent on background image estimation, estimation of target positions are not so sensitive.

Several alternative ways of generating background image are suggested in the literature. One experimental approach is to record image using a phantom that has the same average optical properties as the sample, such as human breast. Along the same line, image of the healthy contralateral breast taken under the same experimental conditions as that of the suspect breast may be used as background image for breast imaging. Some authors have suggested acquiring data at a wavelength for which the target(s) and the background have identical optical properties for assessing the background, e. g., measurement using 805-nm light for which hemoglobin and oxyhemoglobin have the same absorption coefficient may serve as background to image hemoglobin oxygenation. Still another approach is to compute the background using an appropriate forward model. Any of these approaches may be employed for generating the background image for use with the TROT formalism presented here.

The geometries commonly used in DOT include slab, cylindrical, hemispherical, and semi-infinite; and different source-detector combinations have been used to record images in these geometries. As long as multiple source-detector combinations provide multiple angular views of the sample the TROT formalism can be adapted to obtain target location for these geometries. TR imaging and TR-MUSIC was originally developed for reflection (backscattering) geometry that used coincident transceiver array to detect the return signal. With requisite modification in the experimental arrangement, TROT would be suited for use in the reflection geometry.

Example 2 Single Absorptive Target at Different Depths

Figure 3:
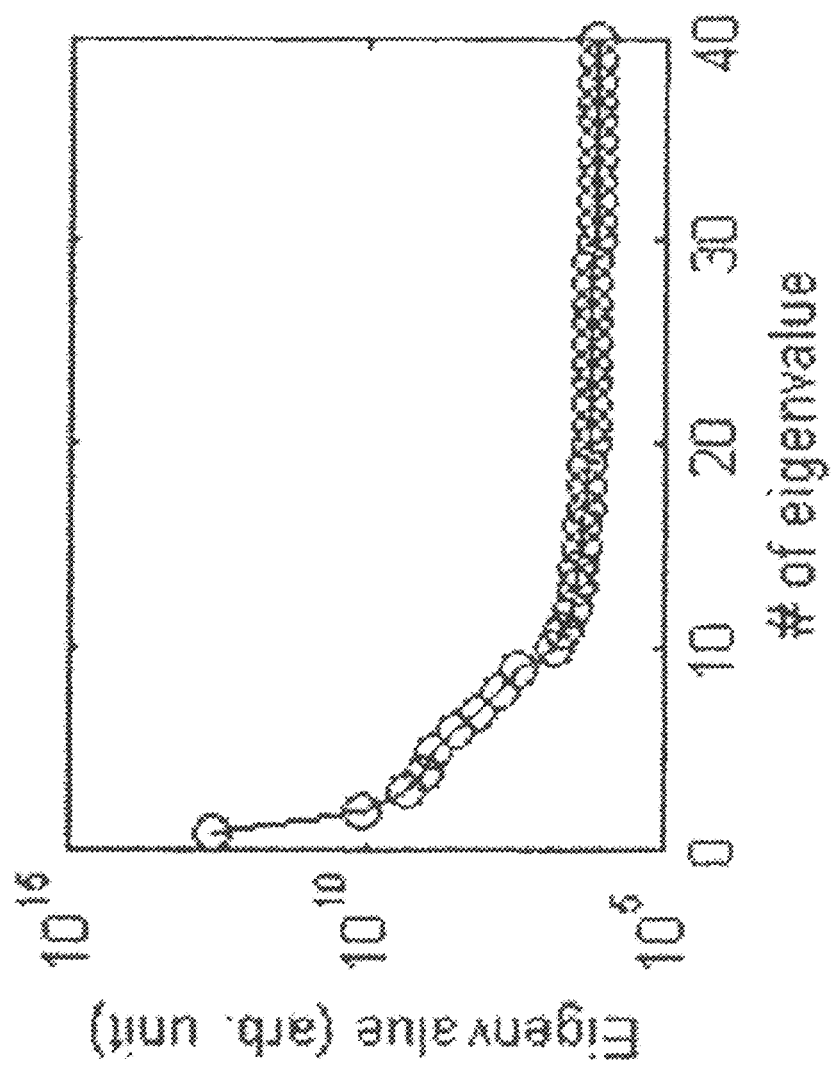
FIG. 3 is a semi-log plot of the first 40 leading eigenvalues for the target at z=30 mm.

In the first experiment, only one target was used, the lateral (x, y) position of the target was kept the same at (25.5 mm, 24.7 mm), while seven different depths (position along z-axis) of 15 mm, 20 mm, 25 mm, 30 mm, 35 mm, 40 mm and 45 mm were used. The eigenvalue spectrum plotted on logarithmic scale for the target at z=30 mm is shown in FIG. 3. Similar eigenvalue spectra were obtained for other cases.

Both SDDS and DSSD pseudo spectra were calculated using Eq. (20). The target was identified as an absorptive target. In the DSSD pseudo spectrum, the absorptive pseudo value at the peak position is ~41 times of the scattering pseudo value associated with $\partial_z g_d$, and even larger than those associated with $\partial_x g_d$ and $\partial_y g_d$, as shown in Table 2. Similarly in the SDDS scheme, the absorptive pseudo value at the peak position is ~33 times of the scattering pseudo value with $\partial_z g_s$, and much larger than the other two.

TABLE 2

Pseudo values associated with absorptive and scattering components at the peak

| Scheme with GFV (g) | Absorptive pseudo value | Scattering pseudo value | | |
|---|---|---|---|---|
| | | $\partial_x g$ | $\partial_y g$ | $\partial_z g$ |
| DSSD ($g_d$) | 1305.0 | 1.0 | 1.0 | 31.7 |
| SDDS ($g_s$) | 2729.3 | 14.0 | 1.1 | 81.6 |

Figure 4:
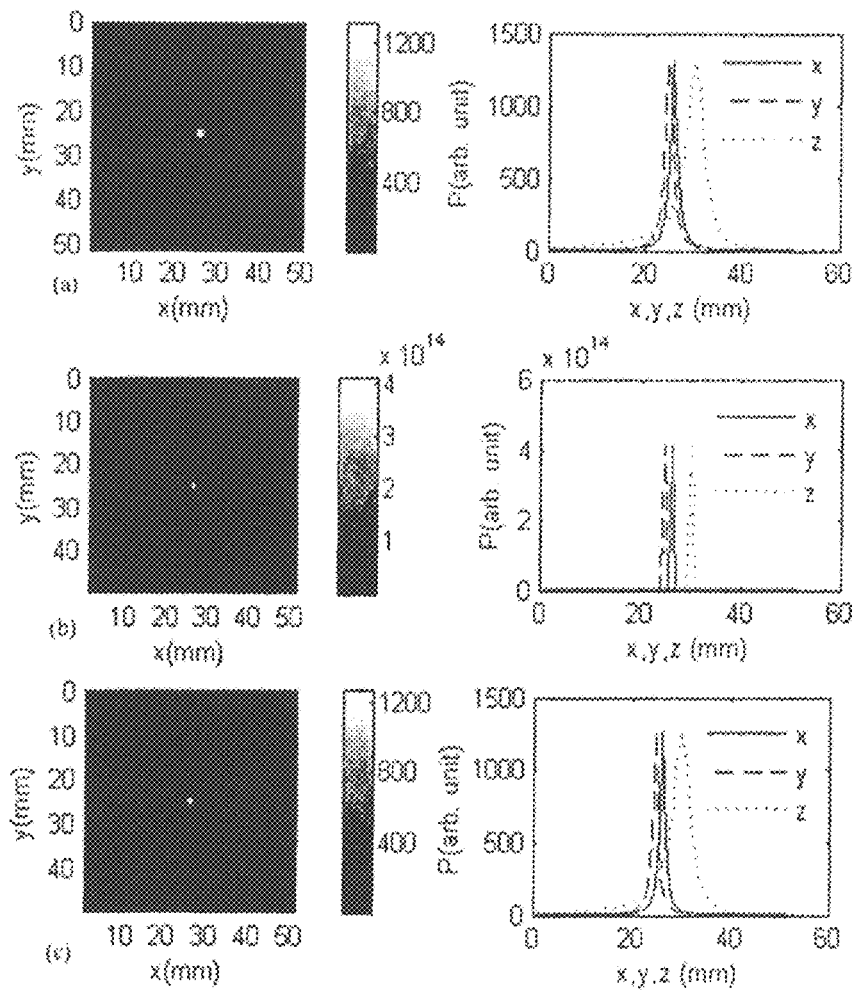
FIG. 4 depicts pseudo image of the target (left pane) and corresponding spatial intensity profiles (right pane) when the target is located at z=30 mm: (a) experimental data; (b) simulation without any added noise; and (c) simulation with 20% Gaussian noise added. The pseudo values are calculated using Eq. (20)

Three-dimensional tomographic images were generated using the whole absorption pseudo spectrum for all voxel positions in the sample. The left pane of FIG. 4 shows a tomographic image for the target at z=30 mm. The spatial profiles in the x, y and z directions, shown in the right pane of FIG. 4 were used to assess the target location. Similar images were generated for other depths. The retrieved target positions are compared with known positions in Table 3.

As is evident from Table 3, when DSSD scheme was used, the TROT-assessed lateral positions (x, y) were within 0.6 mm of the known values, which is an excellent agreement. The accuracy of the z-position was found to be optimal when the target was located in the middle plane of the sample, and deteriorated when the target was closer to the source plane or the detection plane. When using SDDS scheme, the TROT-assessed lateral positions were also within 0.6 mm of the known positions, except for z=40 mm and 45 mm, where the error in y direction was 1.2 mm and 2 mm, respectively. However, remarkable improvement in the accuracy of the z-position estimation was observed, the error $\Delta z$ being within 0.5 mm for all cases except for z=35 mm, where the error was 1.5 mm. We ascribe the superior performance of the scheme using $T_{SDDS}$, to the much larger size of the detector array (1024×1024) than that of the source array (9×9) used in the experimental arrangement.

TABLE 3

Positions of one target located at different depths

| | DSSD Scheme | | SDDS Scheme | |
|---|---|---|---|---|
| Known Positions x, y, z (mm) | Retrieved Positions x, y, z (mm) | Error $\Delta x, \Delta y, \Delta z$ (mm) | Retrieved Positions x, y, z (mm) | Error $\Delta x, \Delta y, \Delta z$ (mm) |
| 25.5, 24.7, 15 | 24.9, 24.4, 17.5 | 0.6, 0.3, 2.5 | 24.9, 25.2, 15.5 | 0.6, 0.5, 0.5 |
| 25.5, 24.7, 20 | 25.7, 24.4, 21.5 | 0.2, 0.3, 1.5 | 24.9, 25.2, 20.5 | 0.6, 0.5, 0.5 |
| 25.5, 24.7, 25 | 25.7, 24.4, 26.5 | 0.2, 0.3, 1.5 | 25.7, 24.4, 24.5 | 0.2, 0.3, 0.5 |
| 25.5, 24.7, 30 | 25.7, 24.4, 30.5 | 0.2, 0.3, 0.5 | 25.7, 25.2, 29.5 | 0.2, 0.5, 0.5 |
| 25.5, 24.7, 35 | 25.7, 25.2, 33.5 | 0.2, 0.5, 1.5 | 24.9, 24.4, 36.5 | 0.6, 0.3, 1.5 |
| 25.5, 24.7, 40 | 24.9, 25.2, 36.5 | 0.6, 0.5, 3.5 | 24.9, 25.9, 40.5 | 0.6, 1.2, 0.5 |
| 25.5, 24.7, 45 | 24.9, 25.2, 39.5 | 0.6, 0.5, 5.5 | 24.9, 26.7, 45.5 | 0.6, 2.0, 0.5 |

FIG. 4, Pseudo image of the target (left pane) and corresponding spatial intensity profiles (right pane) when the target is located at z=30 mm: (a) experimental data; (b) simulation without any added noise; and (c) simulation with 20% Gaussian noise added. The pseudo values are calculated using Eq. (20).

It should be noted that the choice of either DSSD or SDDS scheme depends on experimental parameters, such as, the number and density of sources and detectors, and does not depend on the characteristics of the background medium. When more detectors than sources are used and inter-detector spacing is small, SDDS would provide better resolution than DSSD, and vice versa. However, due to the diffusive nature of light propagation in the turbid medium, increasing the numbers and decreasing the spacing of the sources/detectors beyond a limit may not always improve the results.

While the target position could be obtained from the experimental data, it was observed that the difference between the smaller eigenvalues in the signal subspace and the larger eigenvalues in the noise subspace were not as pronounced as observed in the simulation in Section 4. To assess the effect of noise and to what extent noise may be present in the experimental data, we generated simulated data mimicking the experimental conditions, and added different noise levels. The lateral positions were (25.5 mm, 24.7 mm) and all seven positions (depth) of 15 mm, 20 mm, 25 mm, 30 mm, 35 mm, 40 mm, and 45 mm were tested. Typical pseudo images generated for z=30 mm without and with 20% Gaussian multiplicative noise to compare with the experimental result are shown in FIG. 4. Simulated data provided the known position coordinates.

The simulated spatial profiles with zero added noise are much sharper than the profiles obtained from experimental data, or from simulated data with 20% added Gaussian noise. Broadening of spatial profile is an indication of the uncertainty in determination of position coordinates. Results from simulation show that uncertainty in position determination increases with added noise, and that experimental data behave in a way similar to simulated data with added noise.

Example 3 Resolving Two Absorptive Targets

Figures 5A, 5B, 5C:
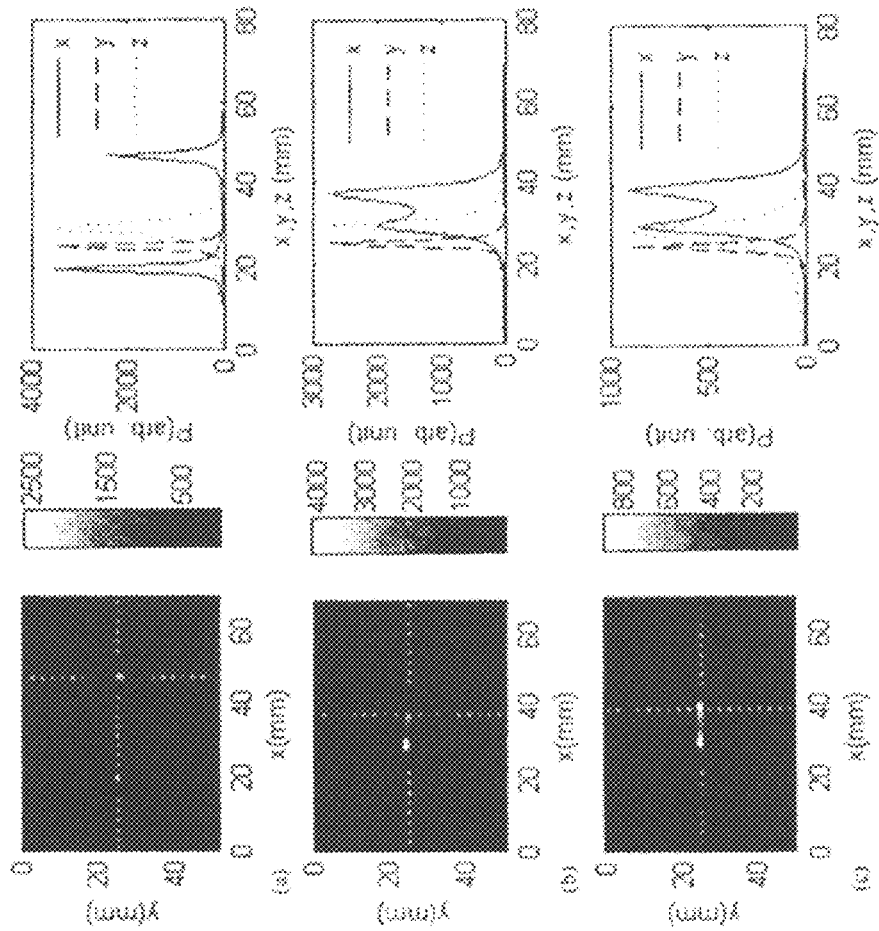
FIG. 5A (Experiment) shows TROT generated cross-section pseudo image when the targets are separated by 27.6 mm is shown in the left pane and pseudo-value profiles through the right target along x, y and z directions are shown in the right pane.
FIG. 5B (Experiment) shows TROT generated cross-section pseudo image when the targets are separated by 12.6 mm is shown in the left pane and the corresponding spatial profiles through the right target along x, y and z directions are shown in the right pane, FIG. 5C (Simulation) shows TROT generated cross-section pseudo image when two targets are separated by 12.6 mm is shown in the left pane and the corresponding pseudo-value profiles are plotted in the right pane. In simulation 10% Gaussian noise is added for comparison with the experimental results. P is pseudo value calculated using Eq. (20)

In the second experiment using two targets the depth (z) and height (y) were kept same (z=30 mm, y=26.0 mm), while three different center-to-center separations, $\Delta x$ of ~12.6 mm, 17.6 mm, and 27.6 mm, between them along the x-axis were considered. A cross-sectional pseudo image of the targets when separated by a center-to-center distance of 27.6 mm, generated using the pseudo spectrum is shown in the left pane of FIG. 5A. FIG. 5B shows a similar image for the separation 12.6 mm (separation between nearest edges ~4 mm). A similar image for the separation 17.6 mm was also obtained (not shown in the figure). The profiles in the x, y and z directions through the right target are shown in the right panes of FIG. 5A, FIG. 5B and FIG. 5C. These profiles were used to assess locations of the targets, and the separation between the two targets. In all cases, the targets were determined to be absorptive, because peaks occurred in the pseudo spectrum with the GFVs corresponding to absorption property.

The known and retrieved positions from the experiments and separations $\Delta x$ between the two targets appear in Table 4. In all the cases, the two targets were resolved, even when their center-to-center separation was 12.6 mm apart, nearest sides separated by only ~4 mm. For all retrieved positions, the maximum error in the lateral positions is 3.0 mm, and the maximum error in the axial positions is 1.5 mm. The errors in the lateral positions increase as the targets get closer. We ascribe this increase in error in the lateral position to the crosstalk between the two targets, the peak due to one target being affected by the other. The shift in the peaks is also affected by noise. When the two targets are very close or significant noise is present, the two peaks merge, so that the two targets are not resolved. This behavior was confirmed in simulations.

The results were compared with simulated data using similar conditions. For the more challenging case of two targets located at z=30 mm and separated by 12.6 mm, exact target locations were found when no noise was added. With 10% noise present, the positions of the two targets were found to be (39.0 mm, 24.8 mm, 29.0 mm) and (30.0 mm, 24.8 mm, 29.0 mm) with target separation 9.0 mm, compared to 12.6 mm (known) and 6.9 mm retrieved from experiment. The pseudo image and the corresponding profiles through the right target are shown in FIG. 5C. Similar images were also obtained for the left target. The retrieved separation between the two targets in simulation with 10% noise was smaller than the actual separation. But the error was less than the experimental result. However, when 20% noise was added, the two peaks merged (not shown here).

TABLE 4

Positions of two targets separated with different distances

| Known Separation [Δx, (mm)] | Target # | Known Position [x, y, z (mm)] | Retrieved Position [x, y, z (mm)] | Error (mm) | Retrieved Separation [Δx, (mm)] |
|---|---|---|---|---|---|
| 12.6 | 1 | 27.6, 26.0, 30 | 30.3, 24.4, 28.5 | 2.7, 1.6, 1.5 | 6.9 |
|  | 2 | 40.2, 26.0, 30 | 37.2, 25.2, 29.5 | 3.0, 0.8, 0.5 |  |
| 17.6 | 1 | 25.1, 26.0, 30 | 26.4, 24.4, 28.5 | 1.3, 1.6, 1.5 | 14.6 |
|  | 2 | 42.7, 26.0, 30 | 41.0, 25.2, 29.5 | 1.7, 0.8, 0.5 |  |
| 27.6 | 1 | 20.1, 26.0, 30 | 19.5, 25.2, 29.5 | 0.6, 0.8, 0.5 | 27.6 |
|  | 2 | 47.7, 26.0, 30 | 47.1, 25.2, 30.5 | 0.6, 0.8, 0.5 |  |

The limits on the size of targets, separation between the targets, and the target-to-background contrast ratio that are needed to detect and locate the targets depend on noise level, experimental parameters (such as, number and concentration of sources and detectors), and ultimately on the diffuse nature of light propagation in the turbid medium. Coordinated experimental work and numerical modeling will be needed to assess those limits.

Example 4 Single Scattering Target at Different Depths

Figures 6A, 6B:
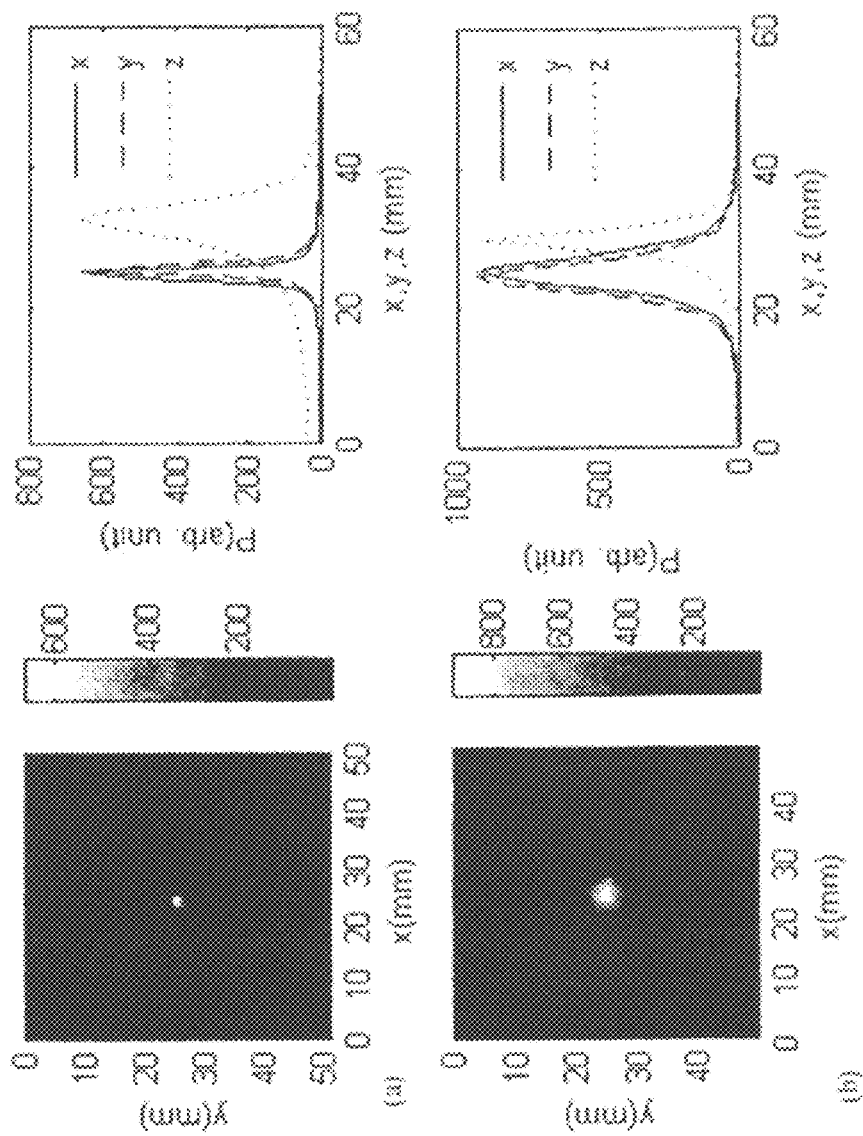
FIG. 6A and FIG. 6B are a pseudo image of target (left pane) and corresponding spatial intensity profiles (right pane) when the target is located at z=30 mm, where

The experiment involving the third sample is the same as the first one except that the target was scattering in nature. The scattering target was a 10-mm diameter glass sphere filled with Intralipid-20% suspension in water, whose concentration was adjusted to provide a mean path of ~0.25 mm, $\mu_s=11.3$ mm$^{-1}$. The same scanning and data acquisition scheme was used as for the absorptive targets and the following z-positions of the target were used: 15 mm, 20 mm, 25 mm, 30 mm, 35 mm, 40 mm, and 45 mm. DSSD scheme was used to calculate the pseudo spectrum. A cross-section pseudo image and the corresponding spatial profiles are displayed in FIG. 6A when z=30 mm. It is compared to the simulation results with 20% Gaussian noise (FIG. 6B). The lateral (x, y) spatial profiles of the pseudo image generated using simulated data are considerably wider, while the axial (z) spatial profile is narrower than those obtained using experimental data, and the peak values from the two cases are of the same order. The retrieved target positions are listed in Table 5. SDDS scheme was also used and provided with similar results.

TABLE 5

Positions of one scattering target located at different depths

| Known Positions [x, y, z (mm)] | Retrieved Positions [x, y, z (mm)] | Error [Δx, Δy, Δz (mm)] |
|---|---|---|
| 25.7, 24.5, 15 | 24.9, 25.9, 18.5 | 0.8, 1.4, 3.5 |
| 25.7, 24.5, 20 | 27.2, 26.7, 20.5 | 1.5, 2.2, 0.5 |
| 25.7, 24.5, 25 | 25.7, 26.7, 23.5 | 0.0, 2.2, 1.5 |
| 25.7, 24.5, 30 | 24.9, 25.2, 32.5 | 0.8, 0.7, 2.5 |
| 25.7, 24.5, 35 | 24.9, 25.2, 36.5 | 0.8, 0.7, 1.5 |
| 25.7, 24.5, 40 | 24.9, 25.9, 41.5 | 0.8, 1.4, 1.5 |
| 25.7, 24.5, 45 | 24.9, 25.9, 45.5 | 0.8, 1.4, 0.5 |

In FIGS. 5A-5C, and more prominently in FIG. 6, the image resolution seems better for experimental data than simulated data. Since the peak values and bandwidth of lines (the poles) in the pseudo spectrum depend strongly on the noise, this difference in image resolution is presumably due to lower noise level in the experiments than that used in simulations.

A comparison of experimental results for scattering and absorptive targets validate the common notion that it is more challenging to locate and image scattering targets than absorptive targets in a highly scattering medium. Also the lateral (x, y) positions are determined with higher accuracy than the axial (z) position. Overall the TROT-retrieved target positions are in good agreement with the known positions.

Discussion

The invention presents the development of time reversal imaging approach with subspace classification, MUSIC in the optical domain. The results from experiment and simulation show that TROT is a faster and less computation intensive approach for detecting small targets in highly scattering turbid media and determining their locations in 3-D than other inverse image reconstruction techniques. While the dominant features in the pseudo spectrum are related to the square of the difference between the absorption (scattering) coefficient of the targets and that of the background, the approach does not directly determine these parameters. It is common for IIR approaches to estimate the optical properties of every voxel in the sample and identify target(s) from differences of these properties between the sample and the target(s), which is a considerably computation intensive undertaking. On the contrary, TROT identifies the targets as poles of the pseudo spectrum and focuses on determining their positions, which do not require as much computation time. Other IIR approaches involve iteration, while TROT is non-iterative. In TROT the data dimension is lower compared to other IIR approaches, which enables analysis and utilization of very large data sets. These two features together make TROT faster. Fast image reconstruction algorithms are of particular interest.

It was observed that lateral (x, y) positions are better determined than the depth (z). Also the spatial profile is more spread out along z compared to that along x, y. We ascribe this difference to fewer data along z-direction compared to those along x-y planes. Addition of another set of data with light incident and signal collected perpendicular to the z-direction is expected to further improve resolution in this dimension. Even without that addition, TROT determines the target position well.

While we have used slab geometry and CW illumination, the TROT approach may be used for other geometries (such as, cylindrical, and spherical), different types of illumination (e.g. frequency domain and pulsed) and different models for light propagation through the medium. Application and adaption of the TROT formalism to inhomogeneous media and extended targets may require careful consideration of several factors. In a non-uniform, inhomogeneous medium, structures other than the desired targets may appear as "false targets" and may interfere with identification of "real targets". However, as long as the contributions to the signal by any false target is smaller than that made by real targets, TROT with MUSIC will be useful in detecting and locating targets, by choosing a proper threshold to separate the signal and noise subspaces. What is even more important, expected wavelength dependence of the target spectroscopic properties could be used to assess the difference between the real and false targets in experiments using multi-wavelength interrogation of the sample.

The TROT formalism presented in this disclosure is particularly suited for point-like targets requiring fewer eigenvectors in the signal subspace to construct a pseudo spectrum. However, for extended finite-size targets, the formalism needs to be modified and much more eigenvectors may be needed to calculate the pseudo spectrum. These interesting problems for further study are currently being pursued.

Example 5—Resolving Fluorescent Targets

Figure 7:
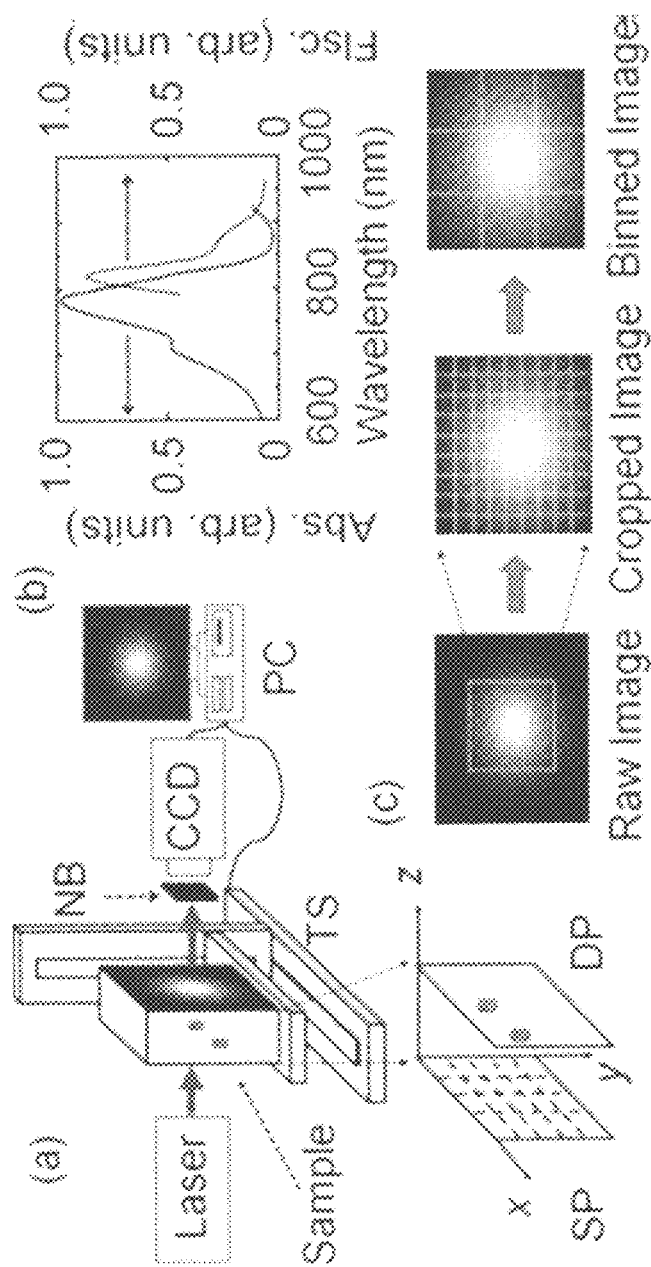
FIG. 7 is a schematic diagram of the experimental arrangement for imaging objects embedded in a turbid medium. [Key: NB=narrow band pass filter (830 nm), TS=translational stage, CCD=charge coupled device, PC=personal computer, SP=source plane, DP=detector plane] Inset (below) shows the 2-D array in the input plane that was scanned across the incident laser beam. A typical raw image is shown in the PC monitor. (b) The absorption and fluorescence spectra of ICG in water. (c) A typical raw image detected by the CCD camera is cropped and binned.

The experimental arrangement, shown schematically in FIG. 7, used a multi-source sample excitation and multi-detector fluorescence signal acquisition scheme to acquire multiple angular views of the sample. The fluorescence light intensities were measured on the boundary of the medium by a two-dimensional detector array when an external point source (laser beam) scanned the other side of the medium. The sample was a 250 mm×250 mm×60 mm rectangular transparent plastic cells filled with Intralipid-20% (Baxter) suspension in distilled water with two fluorescent targets embedded inside. The concentration of Intralipid-20% (background scattering medium) was adjusted to provide a transport mean free path of ~0.99 mm at 790 nm (excitation wavelength), and 1.05 mm at 830 nm (emission wavelength), which were similar to the average value of $l_t$ for human breast tissue. The sample cell thickness of 60 mm was comparable to thickness of a typical compressed breast. The fluorescent targets were two 10-mm long, 4.2 mm inner-diameter cylindrical glass tubes filled with indocyanine green (ICG) dye (Sigma-Aldrich) solution. The dye solution in the targets was prepared by dissolving ICG at a concentration of 1 μM in the Intralipid-20% suspension of same concentration as the background medium to ensure that the targets have the same scattering coefficient as the background medium, but a higher absorption coefficient of 0.027 $mm^{-1}$. ICG is chosen because it absorbs and fluoresces in the NIR enabling deeper penetration of light into tissues, and has been approved by Food and Drug Administration (FDA) for biomedical application. The two targets were embedded in the mid-plane (z=30 mm) of the sample cell.

A 100-mW 790-nm diode laser beam was used to illuminate a 250 mm×250 mm entrance face of the slab sample (source plane). The multi-source illumination scheme was realized by scanning the sample across the laser beam in a 15×11 two-dimensional x-y array of grid points with a step size of 5 mm using a computer-controlled translation stage. A cooled CCD camera equipped with a 60-mm focal-length camera lens collected and sensed a fraction of the fluorescence signal from the opposite face of the sample (detector plane) through a narrow-band (NB) interference filter centered at 830 nm (FWHM 10 nm, 50% transmission). The narrow-band filter was chosen to select a substantial fraction of the ICG fluorescence around the peak emission wavelength and block the scattered 790 nm pump light. The CCD camera had 1024×1024 pixels with a pixel size of 24 μm. The scanning and data acquisition processes were controlled by a personal computer (PC). Each illuminated pixel of the CCD camera could be regarded as a detector. Raw images were recorded by the PC for each scan position, and stored for subsequent analysis. A typical image, which is a 2-D intensity distribution, is shown in the left frame of FIG. 7.

For every scan position, images were also acquired by removing the NB filter that was used to block the pump beam. With the NB filter removed, the recorded images were essentially transillumination images since the fluorescence signal was negligible compared to the much more intense transmission signal (ratio of transmission signal to fluorescence signal ~4500). The experimental arrangement thus enables correlated imaging and retrieval of target location using both fluorescence and transmission measurements. The transmission images were analyzed to estimate the average value of $k=\sqrt{3\mu_a\mu_s'}$ (where $\mu_a$ and $\mu_s'$ are the absorption and reduced scattering coefficients at 790 nm, respectively). The values of these optical parameters of Intralipid-20% suspension in water happened to be very close for excitation and fluorescence wavelengths.

From each fluorescence image, a region of interest was cropped out and then every 5×5 pixels in the cropped image were binned to one pixel to enhance the signal-to-noise ratio. The response data matrix was constructed using the transmitted fluorescence light intensity distribution in these processed images. The TR matrix was generated by multiplying the response matrix by its transpose for our CW probing scheme. The eigenvalue equation of TR matrix was solved.

Figure 8:
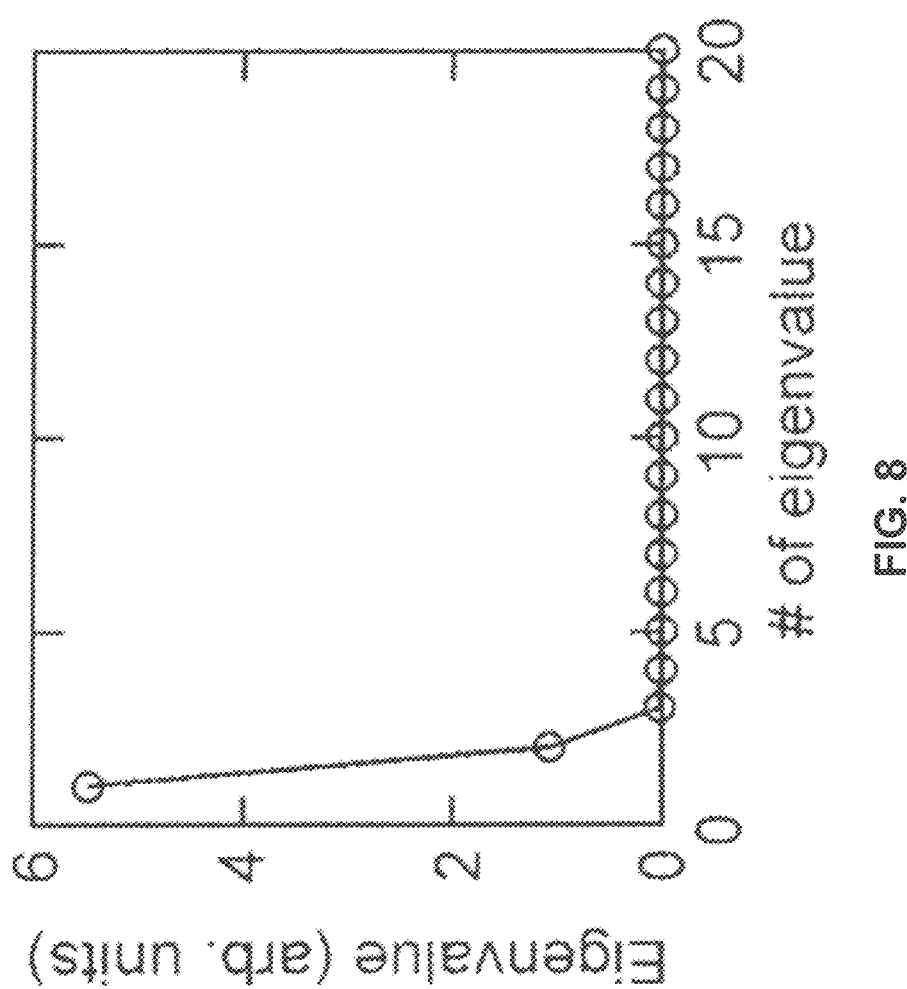
FIG. 8 shows the eigenvalue spectrum of a TR matrix obtained using fluorescence data.
Figure 9:
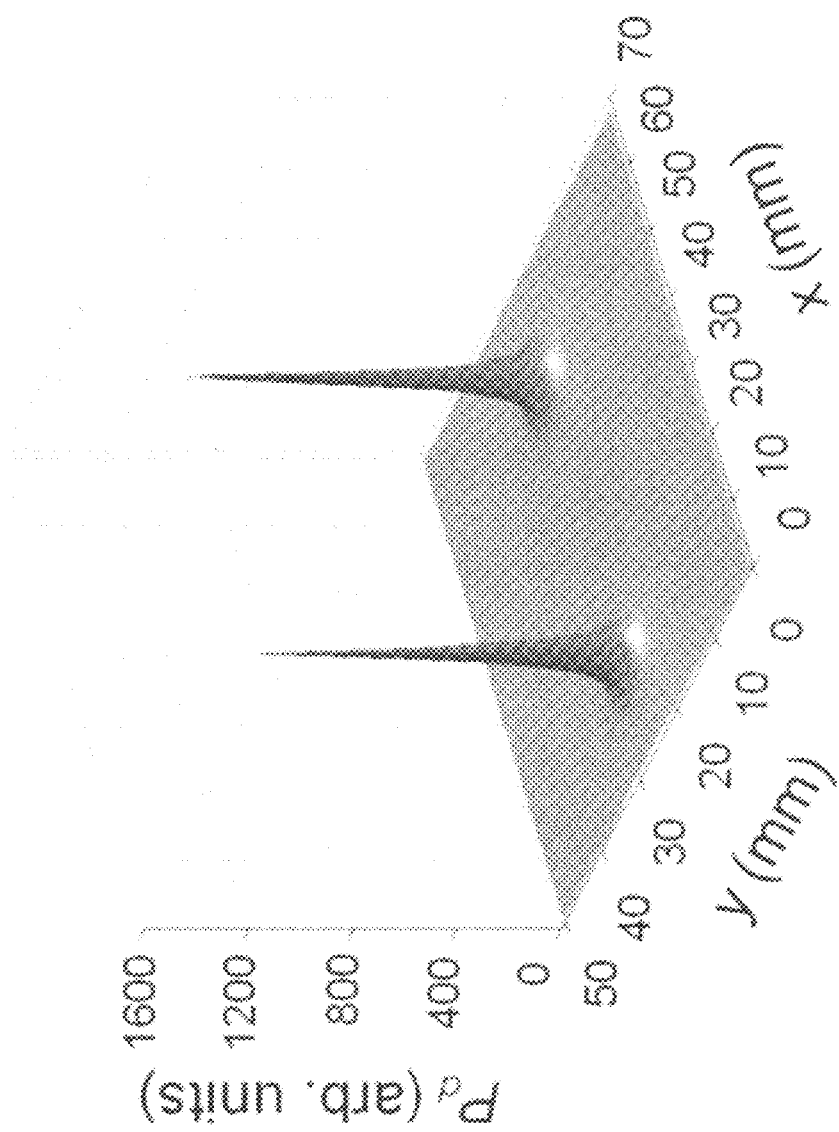
FIG. 9 is a TROT-reconstructed pseudo image at z=29.5 mm using fluorescence data.

The first 20 eigenvalues plotted in FIG. 8 demonstrate that only two eigenvalues are dominant, and consequently those two were included in the signal subspace and separated from the noise subspace. MUSIC algorithm was then used to calculate the pseudo spectrum for all voxels in the 3-D space of the sample. The voxel size was 0.77 mm×0.77 mm×1 mm. Three-dimensional tomographic pseudo images were generated using the pseudo spectrum. FIG. 9 shows one such tomographic image for z=29.5 mm. The single point that the method identifies as the location of a target may be considered to be the "center of fluorescence strength" of the target, which may coincide with the geometrical center for a homogeneous target, but would be weighted by the distribution of fluorescence strength for a heterogeneous target.

TABLE 6

Known and retrieved target positions

| Target | Known positions [x, y, z (mm)] | Retrieved positions [x, y, z (mm)] | | Error [Δx, Δy, Δz (mm)] | |
| --- | --- | --- | --- | --- | --- |
| | | Fluorescence | Transmission | Fluorescence | Transmission |
| Left | 14.2, 25.0, 30.0 | 13.4, 24.9, 29.5 | 12.6, 27.2, 30.5 | 0.8, 0.1, 0.5 | 1.6, 2.2, 0.5 |
| Right | 54.2, 25.0, 30.0 | 53.9, 24.1, 30.5 | 53.9, 27.2, 29.5 | 0.3, 0.9, 0.5 | 0.3, 2.2, 0.5 |

The retrieved positions shown in Table 6 are in good agreement with the known locations of the targets. Further experimentation and simulation reveal that TROT achieves better resolution in the lateral (x, y) directions than in the axial (z) direction, and that the resolution depends on separation between the targets and other experimental parameters. We estimate that under the reported experimental conditions and parameters, the same two targets could be resolved even when the closest lateral (x, y) distance between their surfaces were 2 mm (center-to-center distance of 6 mm) with a noise level of ~10%. If the targets had the same lateral position but different z-positions, the separation between them could be determined within 2 mm even with 50% additive random noise when the separation was 30 mm. As the axial distance between the two targets was reduced to 20 mm, the approach retrieved the separation to be smaller than 20 mm, such as, 18 mm for up to 20% noise, 11 mm for 40% noise, and failed to resolve for 45% or higher noise. For an axial separation of 17 mm the targets could not be resolved even with 0 noise. The axial resolution could be improved if data were acquired in a wider angular view (for example, additional measurements across an adjacent (y-z) side), or using cylindrical geometry.

Example 6 Detecting Tumors in the Model Breast

The optical imaging experiments on the model breast were carried out using a 750 nm near-infrared beam from a Ti:sapphire laser. The average beam power was 10 mW. The light beam was collimated to a 1-mm spot onto the entrance face (henceforth referred to as the 'source plane') of the slab sample. Multiple source illumination was realized in practice by step scanning the slab sample along the horizontal (x) and vertical (y) directions across the laser beam in an x-y array of grid points using a computer controlled translation stage. A camera lens collected the diffusely transmitted light on the opposite face of the sample (henceforth referred to as the 'detection plane') and projected it onto the sensing element of a cooled 16 bit, 1024×1024 charged couple device (CCD) camera. Each illuminated pixel of the 1024× 1024 pixels of the CCD camera could be regarded as a detector. For illumination of every scanned point on the source plane, the CCD camera recorded the diffusely transmitted intensity pattern on the detection plane. A 62.5 mm×37.5 mm area of the source plane was scanned in a 26×16 array of x-y grid points with a step size of 2.5 mm, while the CCD camera imaged the entire detection plane.

The images were cropped with a region of interest within 50 mm×50 mm. Then every 5×5 pixels were binned to one to increase the signal-to-noise ratio. An average image was generated and used to calculate the perturbation due to tumors in the measured light intensity distribution on the sample exit surface. The response data matrix K and the TR matrix T were then constructed. Eigenvalues and eigenvectors of T were calculated. Signal and noise subspaces were separated with a proper threshold level. The pseudo spectrum was then calculated. Global maxima were found to be associated with $\partial_z g_d$, corresponding to scattering targets, i.e. tumors were characterized as scattering targets.

Figure 10A:
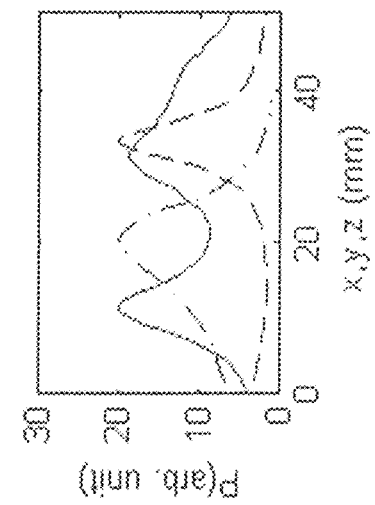
FIG. 10A and FIG. 10C are TROT-generated cross section pseudo images for the left and right tumors using 750 nm laser beam for illumination.
Figure 10B:
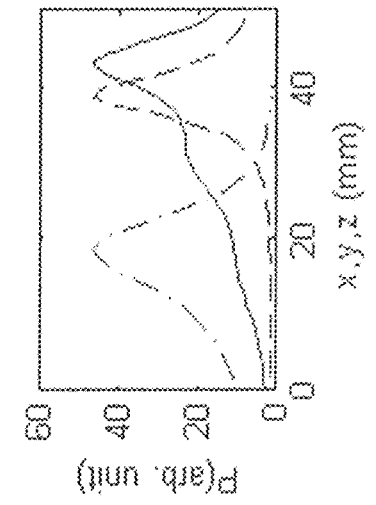
FIG. 10B and FIG. 10D are pseudo value profiles through the target along x(-), y(--) and z(-.) directions.
Figure 10C:
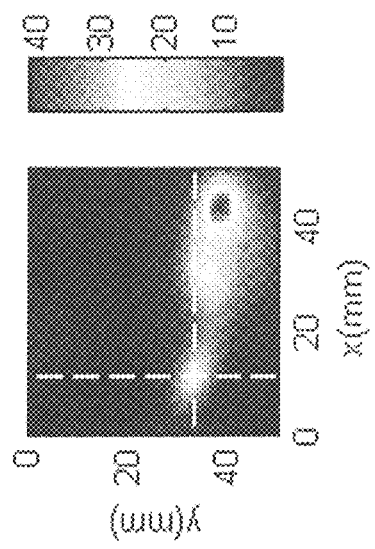
Figure 10D:
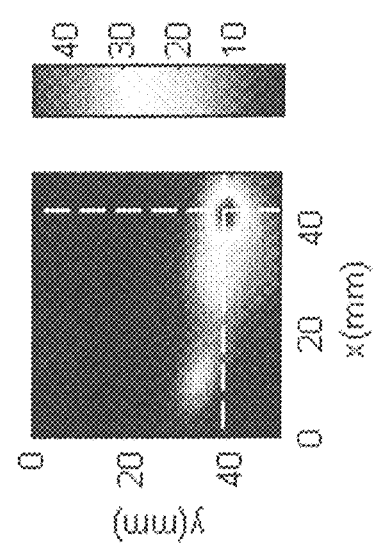

TROT analysis was carried out on the dataset. The TROT-generated cross-section images of the tumors are shown in FIG. 10A and FIG. 10C. Profiles through the tumor position in the x, y and z directions are plotted in FIG. 10B and FIG. 10D.

Figure 11A:
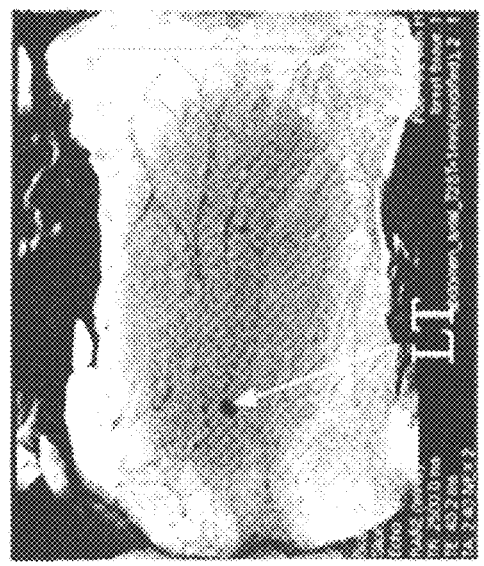
FIG. 11A and FIG. 11B are magnetic resonance images of the left tumor (LT) and the right tumor (RT) pieces.
Figure 11B:
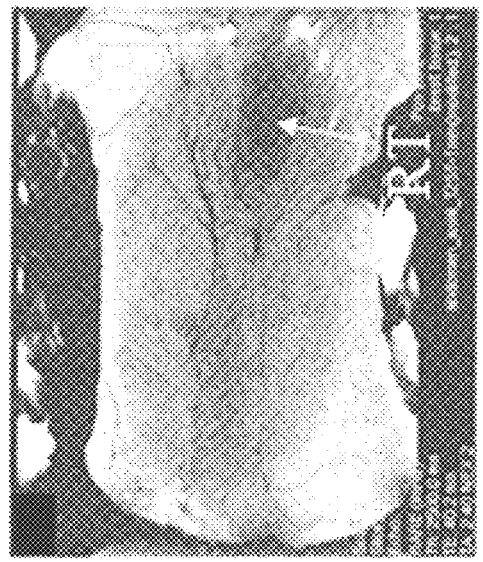

The peaks in the pseudo spectrum (pseudo images) were used to represent the locations of the tumors (targets). The locations of the tumors were retrieved to be (11.5, 33.1, 20.5) mm and (43.4, 38.6, 18.5) mm for the left and right tumors respectively. The left tumor was shown to be much smaller and harder to detect than the right tumor. The distance between the centers of the left and right tumors was found to be ~30 mm. The results are comparable to the MRI images as shown in FIGS. 11A and 11B.

FWHM of the peaks in the pseudo spectrum was used to estimate the dimensions of the tumors. The lateral dimensions of the right tumor were retrieved to be 16.7 mm×8.8 mm, and the left tumor, 7.2 mm×7.6 mm. These retrieved dimensions of both tumors are comparable to the known dimensions of the tumors.

The results showed TROT could detect and localize both tumors. TROT is a fast approach for DOT with no iterations of forward model involved. A priori information of the targets was not used for the approach. Even though, slab geometry, diffusion model and CW measurements were used in this study, TROT is applicable to different geometries, different forward models, and different domains such as frequency domain and time domain. TROT has a potential to be used in real-time breast cancer detection and imaging.

In view of the foregoing, embodiments of the invention provide a computationally efficient optical time reversal method that can be used to image targets in a highly scattered medium. A technical effect is to permit a user to optically image a target, such as a biological issue, in real time without the need to use harmful radiation.

In view of the foregoing, embodiments of the invention provide a computationally efficient optical time reversal method that can be used to image targets in a highly scattered medium. A technical effect is to permit a user to optically image a target, such as a biological issue, in real time without the need to use harmful radiation.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a non-transient computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A time reversal optical tomography method to locate an extended tumor target embedded in a biological tissue, the method comprising sequential steps of:
    illuminating a part of the biological tissue with light from an optical source, wherein the biological tissue comprises normal tissue that forms a background and at least one extended tumor target that defines a quantity of extended tumor targets,
    receiving an optical signal from the biological tissue resulting from the illuminating step, wherein the optical signal comprises perturbations in light intensity due to the extended tumor target, the optical signal being a fraction of light received from the biological tissue;
    constructing, with a computer, a response data matrix K using the optical signal,
    calculating, using the computer, a time reversal (TR) matrix $T=K^\dagger K$, where $K^\dagger$ is an adjoint of the response data matrix K, the TR matrix is of larger rank than the quantity of extended tumor targets;
    calculating eigenvalues and eigenvectors of the response data matrix K, including eigenvectors in signal subspace and noise subspace;
    separating the eigenvectors in signal subspace and noise subspace according to a L-curve regularization protocol that includes steps of plotting the eigenvalues and identifying the signal subspace that exceeds a threshold $\epsilon$, wherein eigenvectors in the signal subspace that exceed the threshold $\epsilon$ are deemed signal subspace eigenvectors;
    dividing the biological tissue into a predetermined number of voxels;
    calculating Green's function vectors (GFVs) both $g_d(X_p)$ and $\partial_\alpha g_d(X_p)$ ($\alpha$=x, y, z) for a test target position $X_p$ at a $p^{th}$ voxel from the predetermined number of voxels, for an absorptive test target, and a scattering test target, respectively;
    computing a pseudo-spectrum using the signal subspace eigenvectors;
    generating a pseudo-image from the pseudo-spectrum;
    providing a location of the at least one extended tumor target by displaying the pseudo-image.

2. The method of claim 1, wherein the light from the optical source has a wavelength between 600 nm and 1500 nm.

3. The method of claim 1, wherein the optical signal has a wavelength between 600 nm and 2000 nm.

4. The method of claim 1, wherein receiving the optical signal comprises receiving the fraction of light transmitted through the biological tissue.

5. The method of claim 1, wherein the TR matrix is full rank.

6. The method of claim 1, wherein the optical signal is a continuous waveform (CW).

7. The method of claim 1, wherein the light from the optical source is a pulsed waveform.

8. The method of claim 1, wherein the optical signal is an amplitude-modulated waveform.

9. The method of claim 1, wherein the optical source is a laser.

10. The method of claim 1, wherein receiving the optical signal comprises receiving the fraction of light reflected off the biological tissue.

11. A time reversal optical tomography method to locate an extended tumor target embedded in a biological tissue, the method comprising steps of:

illuminating a part of the biological tissue with light from an optical source, wherein the biological tissue comprises normal tissue that forms a background and at least one extended tumor target that defines a quantity of extended tumor targets, receiving an optical signal from the biological tissue resulting from the illuminating step, wherein the optical signal comprises perturbations in light intensity due to the at least one extended target, the optical signal being a fraction of fluorescence emitted by the at least one tumor;

constructing, with a computer, a response data matrix K using the optical signal, calculating, using the computer, a time reversal (TR) matrix $T=K^{\dagger}K$, where $K^{\dagger}$ is an adjoint of the response data matrix K, the TR matrix is of larger rank than the quantity of extended tumor targets;

calculating eigenvalues and eigenvectors of the response data matrix K, including eigenvectors in signal subspace and noise subspace;

separating the eigenvectors in signal subspace and noise subspace according to a L-curve regularization protocol that includes a step of identifying the eigenvectors in the signal subspace that exceeds a threshold $\epsilon$;

dividing the biological tissue into a predetermined number of voxels;

calculating Green's function vectors (GFVs) both $g_d(X_p)$ and $\partial_\alpha g_d(X_p)$ ($\alpha=x, y, z$) for a test target position $X_p$ at a $p^{th}$ voxel of the predetermined number of voxels, for an absorptive test target, and a scattering test target, respectively;

computing a pseudo-spectrum using the eigenvectors in the signal subspace that exceeds the threshold $\epsilon$;

generating a pseudo-image from the pseudo-spectrum;

providing a location of the at least one extended tumor target by displaying the pseudo-image.

12. The method as recited in claim 11, wherein the biological tissue is an in vivo human breast.

13. The method as recited in claim 11, wherein the biological tissue is an in vivo human prostate.

14. The method as recited in claim 11, wherein the method consists of non-iteratively performing the step of illuminating, the step of receiving, the step of constructing, the step of calculating, the step of separating, the step of calculating eigenvalues, the step of dividing, the step of calculating Green's functions vectors, the step of computing a pseudo-spectrum, the step of generating a pseudo-image and the step of providing a location.

15. The method as recited in claim 11, wherein the pseudo-spectrum is updated in real time.

16. A time reversal optical tomography method to locate extended fluorescent tumor targets embedded in a biological tissue, the method comprising sequential steps of:

placing the biological tissue under an optical source;

illuminating a part of the biological tissue with light at wavelength $\lambda_x$ from the optical source, wherein the biological tissue comprises normal tissue that forms a background and at least one extended tumor target that defines a quantity of extended tumor targets;

receiving an optical signal from the biological tissue at wavelength $\lambda_m$ resulting from the illumination step, wherein the optical signal comprises perturbations in light intensity due to the at least one extended tumor target, the optical signal being selected from (1) a fraction of the light received from the biological tissue, (2) a fraction of fluorescence emitted by the at least one extended tumor target and (3) combinations thereof;

constructing, with a computer, a response data matrix K using the optical signal, calculating a time reversal (TR) matrix $T=K^{\dagger}K$, where $K^{\dagger}$ is the adjoint of the response data matrix K, the TR matrix is of larger rank than the quantity of extended tumor targets;

calculating the eigenvalues and eigenvectors of the response data matrix K, including eigenvectors in signal subspace and noise subspace;

separating the eigenvectors in signal subspace and noise subspace according to a L-curve regularization protocol that includes a step of identifying the eigenvectors in the signal subspace that exceeds a threshold $\epsilon$;

dividing the biological tissue into a predetermined number of voxels;

calculating Green's function vector (GFVs) $g_d(X_p)$ for a test target position $X_p$ at the $p^{th}$ voxel;

computing a pseudo-spectrum using the eigenvectors in the signal subspace that exceeds the threshold $\epsilon$;

generating a pseudo-image from the pseudo-spectrum;

providing a location of the one or more extended tumor target by displaying the pseudo-image.

17. The method as recited in claim 16, wherein the fraction of fluorescence emitted by the at least one extended tumor target is autofluorescence due to intrinsic fluorophores.

18. The method as recited in claim 16, wherein the optical signal is from an exogenous contrast agent administered to the biological tissue.

19. The method as recited in claim 16, wherein the pseudo-spectrum is updated in real time.

20. The method as recited in claim 16, wherein the biological tissue is an in vivo human breast.

* * * * *